(12) United States Patent
Gois et al.

(10) Patent No.: US 11,884,687 B2
(45) Date of Patent: Jan. 30, 2024

(54) BORONATED MULTIFUNCTIONAL TARGETING DRUG CONJUGATES, THEIR USES AND METHODS FOR THEIR PREPARATION

(71) Applicant: Hovione Scientia Limited, Cork (IE)

(72) Inventors: Pedro Gois, Lisbon (PT); Fabio Santos, Montelavar (PT)

(73) Assignee: Hovione Scientia Limited, Cork (IE)

( * ) Notice: Subject to any disclaimer, the term of this patent is extended or adjusted under 35 U.S.C. 154(b) by 0 days.

(21) Appl. No.: 16/489,884

(22) PCT Filed: Mar. 1, 2018

(86) PCT No.: PCT/GB2018/050534
§ 371 (c)(1),
(2) Date: Aug. 29, 2019

(87) PCT Pub. No.: WO2018/158582
PCT Pub. Date: Sep. 7, 2018

(65) Prior Publication Data
US 2020/0010484 A1 Jan. 9, 2020

(30) Foreign Application Priority Data

Mar. 2, 2017 (PT) ........................................ 109941

(51) Int. Cl.
| | | |
|---|---|---|
| C07F 5/02 | (2006.01) |
| A61K 47/64 | (2017.01) |
| A61K 47/66 | (2017.01) |
| A61K 47/55 | (2017.01) |
| A61K 47/60 | (2017.01) |
| A61K 47/69 | (2017.01) |
| A61K 49/00 | (2006.01) |

(52) U.S. Cl.
CPC .............. *C07F 5/025* (2013.01); *A61K 47/55* (2017.08); *A61K 47/60* (2017.08); *A61K 47/643* (2017.08); *A61K 47/66* (2017.08); *A61K 47/6951* (2017.08); *A61K 49/0039* (2013.01); *A61K 49/0052* (2013.01); *A61K 49/0054* (2013.01); *A61K 49/0056* (2013.01)

(58) Field of Classification Search
CPC ....... C07F 5/025; A61K 47/643; A61K 47/66; A61K 47/55; A61K 47/60; A61K 47/6951; A61K 49/0039; A61K 49/0052; A61K 49/0054; A61K 49/0056
See application file for complete search history.

(56) References Cited

U.S. PATENT DOCUMENTS

| | | |
|---|---|---|
| 2016/0024122 A1 | 1/2016 | Raines et al. |
| 2020/0010484 A1 | 1/2020 | Gois et al. |

FOREIGN PATENT DOCUMENTS

| | | |
|---|---|---|
| EP | 3583109 | 12/2019 |
| JP | 2015505559 A | 2/2015 |
| PT | 109941 | 3/2017 |
| WO | 2013084199 A1 | 6/2013 |
| WO | 2013110005 A1 | 7/2013 |
| WO | 2014121291 A2 | 8/2014 |
| WO | 2014170628 A1 | 10/2014 |
| WO | 2015116774 A1 | 8/2015 |
| WO | 2016166319 A1 | 10/2016 |
| WO | 2018158582 A1 | 9/2018 |

OTHER PUBLICATIONS

Santos et al., Angewandte Chemie, vol. 56, No. 32, pp. 9346-9350, Jun. 8, 2017.*
Adib, Mehdi, et al., "Bridgehead Bicyclo[4.4.0]boron Heterocycles: A One-Pot Four-Component Synthesis of Dibenzo [e,i][1,3,7,2]oxadiazaborecin-8(7H)-ones," Helv. Chim. Acta, 2016, pp. 659-664, vol. 99, Wiley-VHCA AG, Zürich.
Santos, Fábio M.F., et al., "A Three-Component Assembly Promoted by Boronic Acids Delivers a Modular Fluorophore Platform (BASHY Dyes)," Chem. Eur. J., 2016, pp. 1631-1637, vol. 22, Wiley-VCH Verlag Gmbh & Co. KGaA, Weinheim.
Akkapeddi, Padma, et al., "Construction of homogeneous antibody-drug conjugates using site-selective protein chemistry," Chem. Sci., 2016, pp. 2954-2963, vol. 7, The Royal Society of Chemistry.
Anderson, Lindsey N., et al., "Live Cell Discovery of Microbial Vitamin Transport and Enzyme-Cofactor Interactions," ACS Chem. Biol., 2016, pp. 345-354, vol. 11, American Chemical Society.
Ashley, Jonathan D., et al., "Liposomal Bortezomib Nanoparticles via Boronic Ester Prodrug Formulation for Improved Therapeutic Efficacy in Vivo," J. Med. Chem., 2014, pp. 5282-5292, vol. 57, American Chemical Society.
Baker, Stephen J., et al., "Boron-containing inhibitors of synthetases," Chem. Soc. Rev., 2011, pp. 4279-4285, vol. 40, The Royal Society of Chemistry.
Baker, Stephen J., et al. "Therapeutic potential of boron-containing compounds," Future Med. Chem., 2009, pp. 1275-1288, vol. 1, No. 7, Future Science Ltd.

(Continued)

*Primary Examiner* — Alicia L Otton
(74) *Attorney, Agent, or Firm* — Conley Rose. P.C.; Rodney B. Carroll

(57) ABSTRACT

Tri-component multi-functional boronated complexes (B-complexes), featuring reversible covalent bonds, are described, which incorporate a drug; a water-soluble moiety (e.g. polyethylene glycol (PEG) chains, cyclodextrins); and a targeting unit. A B-complex core was assembled in one step, and proved to be stable in different biocompatible conditions, such as human plasma, though reversible for example in the presence of glutathione (GSH). This platform enabled the modular construction of the multifunctional conjugates exhibiting high selectivity towards, for example, folate-receptor-positive MDA-MB-231 cancer cells, having an $IC_{50}$ in the low nanomolar range.

21 Claims, 2 Drawing Sheets

(56) References Cited

OTHER PUBLICATIONS

Cal, Pedro M.S.D., et al., "Cysteine-Selective Reactions for Antibody Conjugation," Angew. Chem. Int. Ed., 2014, pp. 10585-10587, vol. 53, Wiley-VCH Verlag GmbH & Co. KGaA.
Chari, Ravi, V.J., et al., "Antibody-Drug Conjugates: An Emerging Concept in Cancer Therapy," Angew. Chem. Int. Ed., 2014, pp. 3796-3827, vol. 53, Wiley-VCH Verlag GmbH & Co. KGaA.
Ciani, Laura, et al., "Boron as a platform for new drug design," Expert Opin. Drug Discov. [Early Online], 2012, 11 pages, Informa UK, Ltd.
Flagstad, Thomas, et al., "A Four-Component Reaction for the Synthesis of Dioxadiazaborocines," Angew. Chem. Int. Ed., 2015, pp. 8395-8397, vol. 54, Wiley-VCH Verlag GmbH & Co. KGaA.
Glocker, Michael O., et al., "Rheumatoid Arthritis, a Complex Multifactorial Disease: On the Way Toward Individualized Medicine," Medicinal Research Reviews, 2006, pp. 63-87, vol. 26, No. 1, Wiley Periodicals, Inc.
Hanahan, Douglas, et al., "Hallmarks of Cancer: The Next Generation," Cell, Mar. 4, 2011, pp. 646-674, Elsevier Inc.
Kim, Chan Hyuk, et al., "Synthesis of Bispecific Antibodies using Genetically Encoded Unnatural Amino Acids," J. Am. Chem. Soc., 2012, pp. 9918-9921, vol. 134, American Chemical Society.
Kumar, Amit, et al., "Design of a Small-Molecule Drug Conjugate for Prostate Cancer Targeted Theranostics," Bioconjugate Chem., 2016, pp. 1681-1689, vol. 27, American Chemical Society.
Liu, Hong Yan, et al., "Solid-Phase Bioconjugation of Heterobifunctional Adaptors for Versatile Assembly of Bispecific Targeting Ligands," Bioconjugate Chem., 2014, pp. 1511-1516, vol. 25, American Chemical Society.
McEnaney, Patrick J., et al., "Chemically Synthesized Molecules with the Targeting and Effector Functions of Antibodies," J. Am. Chem. Soc., 2014, p. 18034-18043, vol. 136, American Chemical Society.
Montalbano, Francesco, et al., "Discovery of new heterocycles with activity against human neutrophile elastase based on a boron promoted one-pot assembly reaction," Org. Biomol. Chem., 2013, pp. 4465-4472, vol. 11, The Royal Chemical Society.
Montalbano, Fancesco, et al., "Four-Component Assembly of Chiral N-B Heterocyles with a Natural Product-Like Framework," Organic Letters, 2012, pp. 988-991, vol. 14, No. 4, American Chemical Society.
Montalbano, Fancesco, et al., "Phenylalanine Iminoboronates as New Phenylalanine Hydroxylase Modulators," RSC Advances, 2013, 7 pages, The Royal Society of Chemistry.
Rossi, Edmund A., et al., "The Dock-and-Lock Method Combines Recombinant Engineering with Site-Specific Covalent Conjugation to Generate Multifunctional Structures," Bioconjugate Chem., 2012, pp. 309-323, vol. 23, American Chemical Society.
Santos, Fábio M.F., et al., "A Three-Component Assembly Promoted by Boronic Acids Delivers a Modular Flourophore Platform (BASHY Dyes)," Chem. Eur. J., 2016, pp. 1631-1637, vol. 22, Wiley-VCH Verlag GmbH & Co. KGaA.
Sethi, Nilay, et al., "Unravelling the complexity of metastasis—molecular understanding and targeted therapies," Nature Reviews, Oct. 2011, pp. 735-748, vol. 11, Macmillan Publishers Limited.
Sheikh, Saba, et al., "Neurodegenerative Diseases: Multifactorial Conformational Diseases and Their Therapeutic Interventions," Journal of Neurodegenerative Diseases, 2012, 8 pages, vol. 2013, Hindawi Publishing Corporation.
Shin, Weon Sup, et al., "Cancer Targeted Enzymatic Theranostic Prodrug: Precise Diagnosis and Chemotherapy," Bioconjugate Chem., 2016, pp. 1419-1426, vol. 27, American Chemical Society.
Su, Jing, et al., "Catechol Polymers for pH-Responsive, Targeted Drug Delivery to Cancer Cells," J. Am. Chem. Soc., 2011, pp. 11850-11853, vol. 133, American Chemical Society.
Swartz, Melody A., et al., "Tumor Microenviornment Complexity: Emerging Roles in Cancer Therapy," Cancer Res, Mar. 13, 2012, pp. 2473-2480, vol. 72, No. 10, American Association for Cancer Research.
Wu, Suhong, et al., "pH-Responsive Drug Delivery by Amphiphilic Copolymer through Boronate-Catechol Complexation," ChemPlusChem, 2013, pp. 175-184, vol. 78, Wiley-VCH Verlag GmbH & Co. KGaA.
Foreign Communication from a related application—International Search Report and Written Opinion of International Application No. PCT/GB2018/050534, dated Jun. 8, 2018, 11 pages.
Foreign Communication from a related application—International Preliminary Report on Patentability of International Application No. PCT/GB2018/050534, dated May 14, 2019, 20 pages.
Smoum, Reem, et al., "Boron Containing Compounds as Protease Inhibitors," Chem. Rev., 2012, pp. 4156-4220, vol. 112, American Chemical Society.
Japanese Office Action and English Translation, dated Nov. 24, 2021 (13 pages), Japanese Application No. 2019-547506.
Adib, Mehdi et al., "Bridgehead Bicyclo[4.4.0]boron Heterocycles: A One-Pot Four-Component Synthesis of Dibenzo [e,i][1,3,7,2]oxadiazaborecin-8(7H)-ones," Helvetica Chimica Acta, 2016, vol. 99, pp. 659-664.
Hopfl, Herbert et al., "Synthesis and Comparative Study of Three Monomeric Boronates by Spectroscopic Methods and X-ray Crystallography," Canadian Journal of Chemistry, 1998, vol. 76, pp. 1352-1360, NRC Canada.
Cal, Pedro M.S.D. et al., "Site-Selective Installation of BASHY fluorescent dyes to Annexin V for Targeted detection of Apoptotic Cells," Chemical Communications, vol. 53, pp. 368-371, Royal Society of Chemistry.
Farfan, Norberto et al., "Synthesis, Crystal Structures, and quadratic Nonlinear Optical Properties in a Series of Push-Pull Boronate Derivatives," Journal of Materials Chemistry, 2002, vol. 12, No. 10, pp. 2898-2903, Royal Society of Chemistry.
Rodriguez, Mario et al., "Imino Diels-Alder Reaction of Boronates: A new Route to 3,4-dihydroquinolines," Journal of Organometallic Chemistry, 2005, vol. 690, pp. 2975-2988, Elsevier B.V.
Canadian Office Action dated May 19, 2023 (6 pages), Canadian Application No. 3,054,477.

* cited by examiner

BORONATED MULTIFUNCTIONAL TARGETING DRUG CONJUGATES, THEIR USES AND METHODS FOR THEIR PREPARATION

CROSS REFERENCE TO RELATED APPLICATIONS

This application is a filing under 35 U.S.C. 371 of International Application No. PCT/GB2018/050534 filed Mar. 1, 2018, entitled "Boronated Multifunctional Targeting Drug Conjugates, Their Uses and Methods for Their Preparation" which claims priority to Portuguese Patent Application No. 109941 filed Mar. 2, 2017, which applications are incorporated by reference herein in their entirety.

FIELD OF INVENTION

The invention described herein relates to cell targeting drug conjugates, uses thereof, and a method for the preparation of multifunctional constructs suitable for the delivery of an active pharmaceutical ingredient (API) to specific diseased tissue and cells. In particular, the invention relates to cell targeting drug conjugates such as cancer cell targeting drug conjugates (CCTDC), and a method for the construction of cell targeting drug conjugates based on the formation of tri-component (tripodal) boronated complexes.

BACKGROUND

Recent developments in human biology facilitate a clearer understanding of the intricate pathogenesis of complex diseases such as cancer (M. A. Swartz, N. Iida, E. W. Roberts, S. Sangaletti, M. H. Wong, F. E. Yull, L. M. Coussens, Y. A. DeClerck, Cancer Res. 2012, 72, 2473-2480; N. Sethi, Y. Kang, Nat. Rev. Cancer 2011, 11, 735-748; D. Hanahan, R. A. Weinberg, Cell 2011, 144, 646-74), neurodegeneration (S. Sheikh, S. E. Hague, S. S. Mir, *J. Neurodegener. Dis.* 2013, 1-8) or rheumatoid arthritis (M. O. Glocker, R. Guthke, J. Kekow, H. J. Thiesen, *Med. Res. Rev.* 2006, 26, 63-87). In cancer, the evolution of normal cells to a neoplastic state is a multifaceted biological process, in which normal cells acquire capabilities of sustaining proliferative signalling, evading growth suppressors, resisting cell death, enabling replicative immortality, inducing angiogenesis, activating invasion and metastasis (D. Hanahan, R. A. Weinberg, Cell 2011, 144, 646-74). Therefore, the most recent strategies to tackle cancer aim at interrupting one or more of these stages using multifunctional constructs, in which, the biological activity of the individual components is preserved and tuned. Despite being conceptually simple, in practice, the assembly of multifunctional constructs is often hampered by the overwhelming complexity of the synthetic process (W. S. Shin, J. Han, P. Verwilst, R. Kumar, J. H. Kim, J. S. Kim, Bioconjug. Chem. 2016, 27, 1419-1426; E. A. Rossi, D. M. Goldenberg, C. H. Chang, Bioconjug. Chem. 2012, 23, 309-323; H. Y. Liu, P. Zrazhevskiy, X. Gao, Bioconjug. Chem. 2014, 25, 1511-1516; A. Kumar, T. Mastren, B. Wang, J. T. Hsieh, G. Hao, X. Sun, Bioconjug. Chem. 2016, 27, 1681-1689; C. H. Kim, J. Y. Axup, A. Dubrovska, S. A. Kazane, B. A. Hutchins, E. D. Wold, V. V Smider, P. G. Schultz, *J. Am. Chem. Soc.* 2012, 134, 9918-9921; P. J. McEnaney, K. J. Fitzgerald, A. X. Zhang, E. F. Douglass, W. Shan, A. Balog, M. D. Kolesnikova, D. A. Spiegel, *J. Am. Chem. Soc.* 2014, 136, 18034-18043; L. N. Anderson, P. K. Koech, A. E. Plymale, E. V. Landorf, A. Konopka, F. R. Collart, M. S. Lipton, M. F. Romine, A. T. Wright, *ACS Chem. Biol.* 2016, 11, 345-354).

Cancer cell-targeting drug conjugates (CCTDC) are multifunctional constructs that combine the lethality of potent cytotoxic drugs with the targeting ability of specific biomolecules that elicit a high affinity for antigens that are overexpressed in cancer cells (P. Akkapeddi, S.-A. Azizi, A. M. Freedy, P. M. S. D. Cal, P. M. P. Gois, G. J. L. Bernardes, *Chem. Sci.* 2016, 7, 2954-2963). In CCTDC, the linker technology used to connect these functions contributes decisively to the therapeutic usefulness of these constructs. The linker technology needs to enable functionalization of the targeting unit without altering its usual biological role or pharmacokinetic properties, by maintaining the integrity of the conjugate during circulation and by triggering the release of the active drug only upon reaching the target (R. V. J. Chari, M. L. Miller, W. C. Widdison, *Angew. Chemie—Int. Ed.* 2014, 53, 3796-3827; P. M. S. D. Cal, G. J. L. Bernardes, P. M. P. Gois, *Angew. Chem. Int. Ed. Engl.* 2014, 53, 10585-7).

Given these requirements, the linker engineering often contemplates incorporation of reactive handles (moieties capable of being post-functionalised, i.e. once the complex is formed, having the ability to be substituted by further useful or desirable groups or molecules) to selectively attach the drug and the targeting biomolecule, and/or groups that may control the conjugate's physicochemical properties (e.g. PEG) and/or cleavable units that promote the stimulus (e.g. enzymes, pH, GSH) responsive release of the drug at the target (R. V. J. Chari, M. L. Miller, W. C. Widdison, *Angew. Chemie—Int. Ed.* 2014, 53, 3796-3827; P. M. S. D. Cal, G. J. L. Bernardes, P. M. P. Gois, *Angew. Chem. Int. Ed. Engl.* 2014, 53, 10585-7). Hence, linkers often exhibit structures having a high functional density, and their construction involves a series of complex and costly synthetic steps that are typically unsuited for a straightforward structural diversification (R. V. J. Chari, M. L. Miller, W. C. Widdison, *Angew. Chemie—Int. Ed.* 2014, 53, 3796-3827). Therefore, the engineering of composite multifunctional molecules that enable tuning of the properties of the construct by simple variation of the individual properties of their components is highly desirable for the expedient discovery of new, therapeutically useful CCTDCs.

For many years, boron compounds stayed under the radar of medicinal chemists because there are relatively few natural products known to contain this element, and due to a common misconception that boron is intrinsically toxic. However, more recently, it has been shown (S. J. Baker, C. Z. Ding, T. Akama, Y.-K. Zhang, V. Hernandez, Y. Xia, *Future Med. Chem.* 2009, 1, 1275-1288) that boric acid has an $LD_{50}$ of 2660 mg/kg, which is similar to regular table salt at 3000 mg/kg. Nevertheless, prejudice against the use of boron still exists due to an inadequate understanding of the physical properties of boronated molecules, and a lack of synthetic tools to incorporate this element (L. Ciani, S. Ristori, *Expert Opin. Drug Discov.* 2012, 7, 1017-1027).

Despite this, the biological evaluation of organoboron molecules has resulted in two US food and drug administration (FDA) approved drugs: the anticancer drug bortezomib (Btz, Velcade®), which is a potent proteasome inhibitor for the treatment of myeloma and lymphoma, and the antifungal agent tavaborole (KERYDIN®), and several other drugs are now at various stages of clinical development (S. J. Baker, C. Z. Ding, T. Akama, Y.-K. Zhang, V. Hernandez, Y. Xia, *Future Med. Chem.* 2009, 1, 1275-1288).

In organic molecules, boron is typically present in the form of neutral planar trivalent boronic acid (BA) having five electrons in the valence shell. In this form, boron has a vacant p-orbital that can readily form dative bonds with oxygen and nitrogen nucleophiles, which converts it from a trigonal-planar structure to an anionic tetrahedral geometry (S. J. Baker, J. W. Tomsho, S. J. Benkovic, *Chem. Soc. Rev.* 2011, 40, 4279-4285). The pKa of the BA functionality typically ranges from 7-9, and is often uncharged at physiological pH (S. J. Baker, C. Z. Ding, T. Akama, Y.-K. Zhang, V. Hernandez, Y. Xia, *Future Med. Chem.* 2009, 1, 1275-1288).

BAs are moderately strong Lewis acids, readily forming reversible covalent complexes with molecules containing vicinal Lewis base donors like proteins, sugars or amino acids (R. Smoum, A. Rubinstein, V. M. Dembitsky, M. Srebnik, *Chem. Rev.* 2012, 112, 4156-4220). Unfortunately, this unspecific reactivity confers unfavourable pharmacokinetic and off-target toxicity to BAs. For instance, Btz does not reach its true therapeutic potential due to dose-limiting side effects, in particular, peripheral neuropathy and thrombocytopenia. Therefore, the emergence of new boronated drugs, especially for anti-cancer applications, dramatically depends on the discovery of an effective strategy to selectively deliver BAs to cancer cells.

In recent years have been disclosed three methodologies aimed at improving the delivery of Btz to cancer cells; all of these involve the immobilization of the drug onto polymers or liposome based vehicles. One system involved a pH-sensitive polymeric carrier based on the well-known conjugation and pH-dependent release of BAs with catechols (J. Su, F. Chen, V. L. Cryns, P. B. Messersmith, *J. Am. Chem. Soc.* 2011, 133, 11850-11853). This system displayed a lower activity against proteasome inhibition than the free drug, and only 30% Btz was released at pH 7.4. This fact motivated the design of a Btz-catechol amphiphilic copolymer system exhibiting enhanced Btz release at pH 5-6, although the constructs also proved less active than the free drug (S. Wu, R. Qi, H. Kuang, Y. Wei, X. Jing, F. Meng, Y. Huang, *Chempluschem* 2013, 78, 175-184). More recently, a liposomal nanoparticle in which Btz was immobilized via a N-alkylic iminodiacetic acid was developed (J. D. Ashley, J. F. Stefanick, V. A. Schroeder, M. A. Suckow, T. Kiziltepe, B. Bilgicer, *J. Med. Chem.* 2014, 57, 5282-5292), yet this was still less active than the free drug.

In a different therapeutic area and using different therapeutic cargo, Montalbano et al (*Org. Biomol. Chem.* 2013 (11) 4465-72) described the use of a boron-promoted one-pot assembly reaction in order to research enzyme inhibitors of human neutrophile elastase (HNE). This work was based on components such as salicylaldehyde, aryl boronic acid and amino acids. Similar work is disclosed in patent specification no. WO 2013/084199. However, the need for targeting therapeutic cargo, such as Btz, for delivery, for example, to cancer cells was not addressed.

BAs readily establish reversible covalent bonds with Schiff base ligands to yield boronated complexes (B-complexes), featuring a modular and reversible tri-component (sometimes referred to as tripodal) framework (T. Flagstad, M. T. Petersen, T. E. Nielsen, *Angew. Chemie—Int. Ed.* 2015, 54, 8395-8397). This strategy has been used in relation to a variety of heterocycles, isosteres of natural products (F. Montalbano, N. R. Candeias, L. F. Veiros, V. André, M. T. Duarte, M. R. Bronze, R. Moreira, P. M. P. Gois, *Org. Lett.* 2012, 14, 988-991), inhibitors/modulators of important human enzymes (F. Montalbano, N. R. Candeias, L. F. Veiros, V. André, M. T. Duarte, M. R. Bronze, R. Moreira, P. M. P. Gois, *Org. Lett.* 2012, 14, 988-991; F. Montalbano, J. Leandro, G. D. V. F. Farias, P. R. Lino, R. C. Guedes, J. B. Vicente, P. Leandro, P. M. P. Gois, *RSC Adv.* 2014, 4, 61022-61027), and fluorescent compounds (BASHY). For example, one of the present inventors, Santos (et al, see *Chem Eur J* (2016) 22 1631-7) used boronic acid salicylidenehydrazone (BASHY) fluorescent dyes, in the module assembly of boronic acids with Schiff base ligands. In particular, these featured an N,N-diethylamino substituent. However, again, the need for targeting therapeutic cargo, such as Btz, for delivery, for example, to cancer cells was not addressed.

Accordingly, the present inventors proposed that certain B-complexes, which display suitable properties of stability and controlled reversibility in biological settings, could be used as a platform to design multifunctional constructs to selectively target and deliver cargo to cells such as cancer cells. Furthermore, it is desired to deliver cargo comprising not only an API (such as Btz) but also alternative or additional agents for the treatment, prophylaxis, diagnosis, prognosis of a disease such as cancer, whether or not the agent itself comprises a B-containing molecule, by appropriate design of such multifunctional constructs.

GENERAL DISCLOSURE OF THE INVENTION

Complexes

By multifunctional constructs hereinbelow is meant molecules that exhibit a complex structure, optionally amenable to post-functionalization, preparable from independent components that have useful (e.g. biological) properties, wherein the multifunctional construct preserves such properties, which complexes are either stimulus-responsive (i.e. able to respond to a chemical stimulus by releasing one or more of such useful components), e.g. CCTDC, or are adapted for post-functionalisation to another such multifunctional complex, preferably one that has useful biological properties and is stimulus-responsive.

The chemical stimulus is suitably one present in a biological medium comprising the construct in use and adjacent the desired target. The chemical stimulus is therefore predetermined according to the environment of the desired target. For example, when the multifunctional construct is a CCTDC, then GSH, which is in a higher concentration in an intratumoural environment, can hydrolyse multifunctional constructs having (as linkers) hydrolysable covalent bonds which attach their components to a B-complex core or to each other.

The multifunctional constructs of this invention are based on a core boronated compound of the general formula (in which the optional ring systems are defined to the right of the dotted line and the substituents are as defined below):

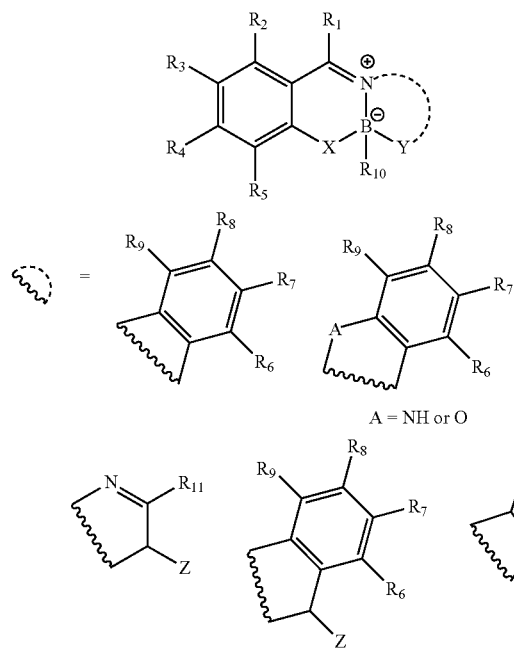

A = NH or O

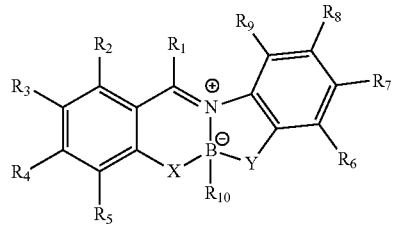

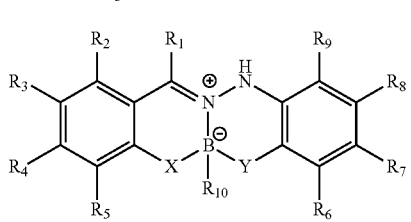

Figure 1:
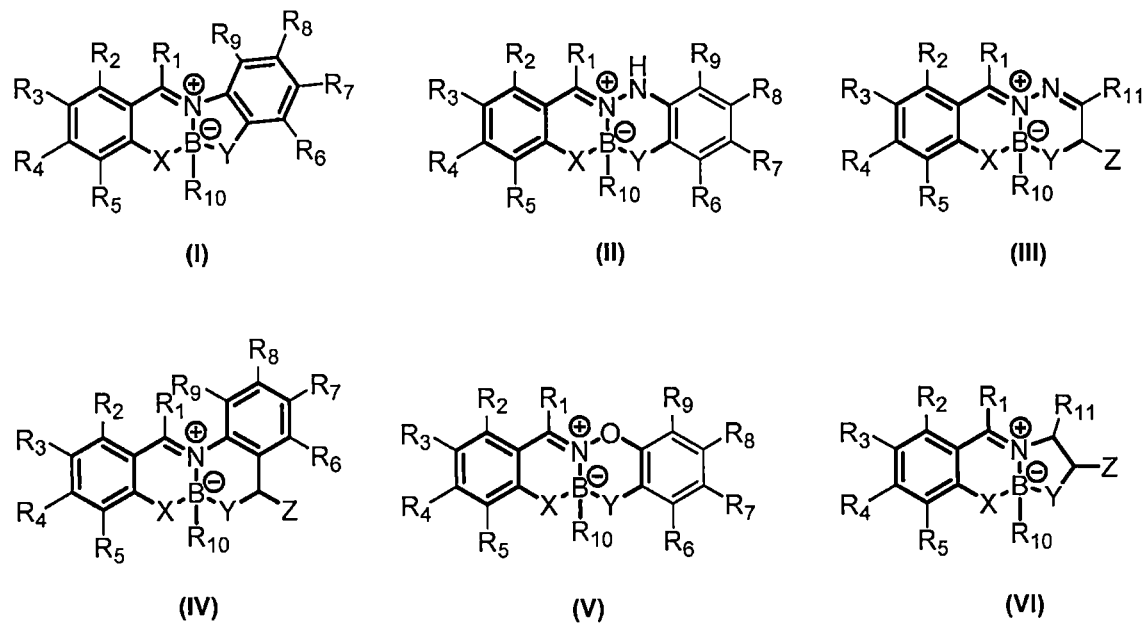
FIG. 1: Preferred core boron compounds for the construction of multifunctional constructs.

The invention described herein provides cell targeting drug conjugates, uses thereof and a method for the construction of multifunctional constructs for the delivery of therapeutic useful cargo to specific diseased tissue and cells based on boronated compounds of the formula (I to VI) shown in FIG. 1. Accordingly, the multifunctional constructs of the invention are based on a core boronated compound of any one of the formulae (I to VI) shown in FIG. 1. In these constructs, the core boron compound enables the assembly or preparation of the multifunctional complex of the invention and controls its reversibility (i.e. disassembly under appropriate biological or chemical conditions by breaking of relevant covalent bonds).

The present invention therefore provides a core boron compound (also referred to as a core B-complex or core complex) of the above general formula, or alternatively any one of the formulae (I to VI), for use in the preparation of a multifunctional construct of the invention:

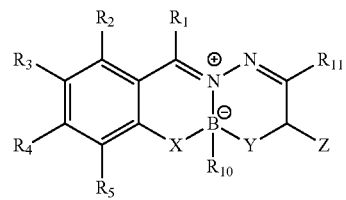
(I)

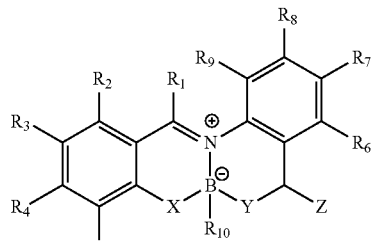
(II)

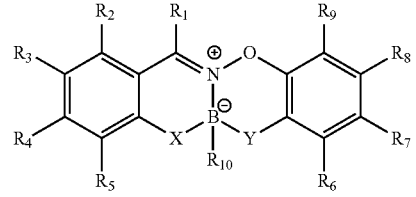
(III)

(IV)

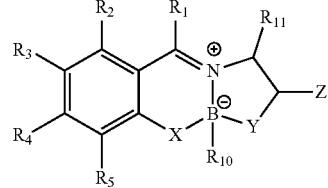
(V)

(VI)

In these formulae: $R_1$ represents H, $C_{n=1-6}$ alkyl, alkene or alkyne which can be straight, branched or cyclic and optionally contain one or more heteroatoms selected from nitrogen, oxygen and sulphur; formyl or $C_{n=2-6}$ alkanoyl; or Ar, $CH_2Ar$ or $CH_2CH_2Ar$, in which the Ar group may be optionally a phenyl, a Cl-, Br- or F-substituted phenyl ring in the o-, m- or p-positions, a naphthyl, a heterocyclic ring or fused ring comprising at least one ring heteroatom selected from nitrogen, oxygen and sulphur.

$R_2$ to $R_5$ represents H, $C_{n=1-6}$ alkyl, alkene or alkyne which can be straight, branched or cyclic and optionally contain one or more heteroatoms selected from nitrogen, oxygen and sulphur; formyl or $C_{n=2-6}$ alkanoyl; amide; ester; Ar, $CH_2Ar$ or $CH_2CH_2Ar$ in which the Ar group may be optionally a phenyl, a Cl-, Br- or F-substituted phenyl ring in the o-, m- or p-positions, a naphthyl, a heterocyclic ring or fused ring comprising at least one ring heteroatom selected from nitrogen, oxygen and sulphur, OH, $OCH_3$, $OCH_2CH_3$, $OCHCH_3CH_3$, $OCH_2CHCH_3CH_3$, OPh, CCH, CCPh, CN, COOH, $NH_2$, CONHR' NHR' or NR'R" in which the R' and R" groups may be optionally a phenyl or a substituted phenyl, a 5 or 6 member azacyclic ring, $C_{n=1-6}$ alkyl which optionally may incorporate one further heteroatom selected from oxygen, sulphur and nitrogen.

$R_6$ to $R_9$ represents H, $C_{n=1-6}$ alkyl, alkene or alkyne which can be straight, branched or cyclic and optionally contain one or more heteroatoms selected from nitrogen, oxygen and sulphur; formyl or $C_{n=2-6}$ alkanoyl; amide; ester; Ar, $CH_2Ar$ or $CH_2CH_2Ar$ in which the Ar group may be optionally a phenyl, a Cl-, Br- or F-substituted phenyl ring in the o-, m- or p-positions, a naphthyl, a heterocyclic ring or fused ring comprising at least one ring heteroatom selected from nitrogen, oxygen and sulphur, OH, OCH$_3$, OCH$_2$CH$_3$, OCHCH$_3$CH$_3$, OCH$_2$CHCH$_3$CH$_3$, OPh, CCH, CCPh, CN, COOH, NH$_2$, CONHR' NHR' or NR'R" in which the R' and R" groups may be optionally a phenyl, a Cl-, Br- or F-substituted phenyl ring in the o-, m- or p-positions, a 5 or 6 member azacyclic ring, C$_{n=1-6}$ alkyl which optionally may incorporate one further heteroatom selected from oxygen, sulphur and nitrogen.

R$_{10}$ represents H, C$_{n=1-6}$ alkyl, alkene or alkyne which can be straight, branched or cyclic and optionally contain one or more heteroatoms selected from nitrogen, oxygen and sulphur; a vinyl group of the general formula CH=CHR' in which the R' represents a H, C$_{n=1-6}$ alkyl, alkene or alkyne which can be straight, branched or cyclic and optionally contain one or more heteroatom selected from nitrogen, oxygen and sulphur, a phenyl or a Cl-, Br- or F-substituted phenyl ring in the o-, m- or p-positions, a naphthyl, a monocyclic or bicyclic heterocyclic ring comprising at least one ring heteroatom selected from nitrogen, oxygen and sulphur; a phenyl or a Cl-, Br- or F-substituted phenyl ring in the o-, m- or p-positions; a naphthyl; or a monocyclic or bicyclic heterocyclic ring comprising at least one ring heteroatom selected from nitrogen, oxygen and sulphur.

R$_{11}$ represents H, C$_{n=1-6}$ alkyl, alkene or alkyne which can be straight, branched or cyclic and optionally contain one or more heteroatoms selected from nitrogen, oxygen and sulphur; formyl or C$_{n=2-6}$ alkanoyl; amide; esters; Ar, CH$_2$Ar or CH$_2$CH$_2$Ar in which the Ar group may be optionally a phenyl, a Cl-, Br- or F-substituted phenyl ring in the o-, m- or p-positions, a naphthyl, a heterocyclic ring or fused ring comprising at least one ring heteroatom selected from nitrogen, oxygen and sulphur; OH; OCH$_3$; OCH$_2$CH$_3$, OCHCH$_3$CH$_3$, OCH$_2$CHCH$_3$CH$_3$, OPh; CCH; CCPh; CN; COOH; NH$_2$; CONHR', NHR' or NR'R" in which the R' and R" groups may be optionally a phenyl, a Cl-, Br- or F-substituted phenyl ring in the o-, m- or p-positions, a 5 or 6 member azacyclic ring, or C$_{n=1-6}$ alkyl, alkene or alkyne which can be straight, branched or cyclic and optionally contain one or more heteroatoms selected from nitrogen, oxygen and sulphur.

X and Y each independently represent a heteroatom selected from oxygen or nitrogen.

Z represents a double bond with oxygen or nitrogen, or a simple bond with H, C$_{n=1-6}$ alkyl, alkene or alkyne which can be straight, branched or cyclic and optionally contain one or more heteroatoms selected from nitrogen, oxygen and sulphur; formyl or C$_{n=2-6}$ alkanoyl; Ar, CH$_2$Ar or CH$_2$CH$_3$Ar in which the Ar group may be optionally a phenyl, a Cl-, Br- or F-substituted phenyl ring in the o-, m- or p-positions, a naphthyl, a heteroaromatic ring or fused ring comprising at least one ring heteroatom selected from nitrogen, oxygen and sulphur; OH; OCH$_3$, OCH$_2$CH$_3$, OCHCH$_3$CH$_3$; OCH$_2$CHCH$_3$CH$_3$; OPh; CCH; CCPh; CN; COOH; NH$_2$, CONHR', NHR' or NR'R" in which the R' and R" groups may be optionally a phenyl, a Cl-, Br- or F-substituted phenyl ring in the o-, m- or p-positions, a 5 or 6 member azacyclic ring, or C$_{n=1-6}$ alkyl, alkene or alkyne which can be straight, branched or cyclic and optionally contain one or more heteroatoms selected from nitrogen, oxygen and sulphur.

The core complexes can be used, or the building blocks (components) used in their preparation can be adapted, to form a multifunctional complex of the invention, in which, in the formulae above, one or more of the R1 to R10 and Z substituents are further selected from one or more multifunctional component(s) comprising:
  a. at least one therapeutically useful cargo molecule, or a residue thereof such that, on breaking at least one covalent bond of the compound, the complete cargo molecule is released;
  b. at least one water-soluble moiety (e.g. polyethylene glycol (PEG) chains, cyclodextrins) or a residue of a water-soluble molecule;
  c. at least one functionalizing moiety capable of being post-functionalised (e.g. with a targeting unit); and/or
  d. at least one targeting unit or a residue of a targeting molecule in which any residue of a molecule is such that, on breaking at least one covalent bond of the multifunctional compound, the complete molecule is released Therefore, the present invention further provides:

A multifunctional compound comprising a tripodal boron core having one or more substituents selected from:
  a. at least one therapeutically useful cargo molecule, or a residue thereof;
  b. at least one water-soluble moiety or a residue of a water-soluble molecule;
  c. at least one functionalizing moiety capable of being post-functionalised; and/or
  d. at least one targeting unit or a residue of a targeting molecule in which any residue of a molecule is such that, on breaking at least one covalent bond of the multifunctional compound, the complete molecule is released.

In some cases, such as when the therapeutic cargo itself comprises a B-atom (as in the case of Btz), then the relevant substituent on R$_{10}$ will be the residue of that therapeutic cargo molecule such that, on breaking of covalent bonds linking components of the complex, the full (complete, intact) cargo molecule (e.g. Btz) is released. Similar considerations apply in relation to the therapeutic cargo molecule when in another position (than R$_{10}$) on the complex core. Similar considerations apply mutatis mutandis to the other components (a) to (d) above vis a vis the actual values for the substituents in any position on the complex core Therefore, throughout this specification, unless the context clearly indicates otherwise, reference to these components will therefore be taken to include or to mean such residues thereof In relation to the multifunctional complexes of the invention, the term therapeutically useful cargo is meant to include drugs or active pharmaceutical ingredients (APIs), radioimaging agents, contrast media and fluorescent moieties, and other agents useful in the therapy, treatment, prophylaxis, diagnosis or prognosis of a medical or pharmacological disease or condition, or the like. Throughout this specification, unless the context indicates otherwise, these terms are used interchangeably.

In the multifunctional complexes of the invention, preferably more than one of the multifunctional substituents [(a) to (d)] are present. More preferably, the multifunctional complex of the invention incorporates either two or three of the multifunctional substituents. Especially preferred is when the multifunctional complex of the invention incorporates:
  a. at least one therapeutically useful cargo molecule; and
  b. at least one water-soluble moiety (e.g. polyethylene glycol (PEG) chains, cyclodextrins); and
  at least one of components (c) and (d) wherein c. is at least one functionalizing moiety capable of being post-functionalised (e.g. with a targeting unit); and (d) is at least one targeting unit.

It will be understood by the person skilled in the art that not only are the core complexes for use as intermediates to the formation (or production) of the multifunctional complexes of the invention, but also many of the multifunctional complexes of the invention are themselves suitable for use as intermediates to other multifunctional complexes of the invention. In particular, a multifunctional complex incorporating component (b) wherein, in any one of the formulae (I) to (VI) above, one or more of R1 to R9, R11, Z is a polyethylene glycol chain may be functionalised to form a multifunctional complex incorporating both components (b) and (c), i.e. to a multifunctional complex wherein one or more of R1 to R9, R11, Z is a polyethylene glycol chain comprising azide, alkyne, alkene or maleimide.

For example, the polyethylene glycol chain optionally comprising azide, alkyne, alkene or maleimide ($H_2C_2(CO)_2NH$)-derived functions, may optionally be selected from PEG-azide wherein a O atom from the PEG chain is replaced by $N_3$ (azide) such as of formula: $R_x$-[—O—(—$CH_2$)$_2$-]$_3$—O— in which $R_x$ is a $C_{1-6}$ alkyl chain end-substituted by an azide ($N_3$) group, or PEG-maleimide wherein an O atom from the PEG chain is replaced by a maleimide group, such as ((1R,8S,9s)-bicyclo [6.1.0]non-4-yn-9-yl)methyl (2-(2-(2-(2-(2,5-dioxo-2,5-dihydro-1H-pyrrol-1-yl)ethoxy)ethoxy)ethoxy)ethyl)carbamate of formula:

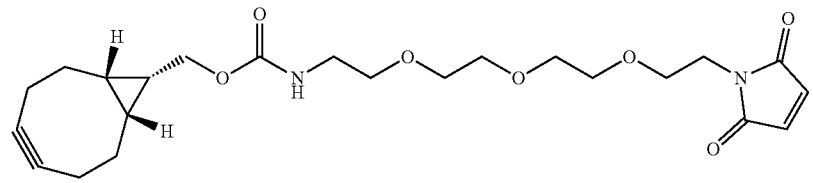 [SMILES: O=C(NCCOCCOCCOCCN1C(=O)C=CC1=O)OC[C@@H]1[C@@H]2CCC#CCC[C@@H]21]

Accordingly, the present invention optionally provides a complex of formula (I to VI), wherein:

$R_1$ represents in compounds I to VI: H, $CH_3$, C1-C6 alkyl which optionally may incorporate heteroatoms selected from nitrogen, oxygen and sulphur, a polyethylene glycol chain comprising azide, alkyne, alkene or maleimide derived functions, formyl or C2-C6 alkanoyl, $CH_2Ar$ or $CH_2CH_2Ar$ in which the Ar group may be optionally a phenyl, a substituted phenyl ring, a naphthyl, a heteroaromatic ring or fused ring comprising at least one ring heteroatom selected from nitrogen, oxygen and sulphur.

$R_2$ to $R_5$ represents in compounds I to VI: H, $CH_3$, C1-C6 alkyl which optionally may incorporate heteroatoms selected from nitrogen, oxygen and sulphur, a polyethylene glycol chain comprising azide, alkyne, alkene or maleimide derived functions, formyl or C2-C6 alkanoyl, amide, esters, $CH_2Ar$ or $CH_2CH_2Ar$ in which the Ar group may be optionally a phenyl, a substituted phenyl ring, a naphthyl, a heteroaromatic ring or fused ring comprising at least one ring heteroatom selected from nitrogen, oxygen and sulphur, OH, $OCH_3$, $OCH_2CH_3$, $OCHCH_3CH_3$, $OCH_2CHCH_3CH_3$, OPh, CCH, CCPh, CN, COOH, $NH_2$, CONHR' NHR' or NR'R" in which the R' and R" groups may be optionally a phenyl or a substituted phenyl, a 5 or 6 member azacyclic ring, $CH_3$, C1-C6 alkyl which optionally may incorporate one further heteroatom selected from oxygen, sulphur and nitrogen.

$R_6$ to $R_9$ represents in compounds I, II, IV and V: H, $CH_3$, C1-C6 alkyl which optionally may incorporate heteroatoms selected from nitrogen, oxygen and sulphur, a polyethylene glycol chain comprising azide, alkyne, alkene or maleimide derived functions, formyl or C2-C6 alkanoyl, amide, esters, $CH_2Ar$ or $CH_2CH_2Ar$ in which the Ar group may be optionally a phenyl, a substituted phenyl ring, a naphthyl, a heteroaromatic ring or fused ring comprising at least one ring heteroatom selected from nitrogen, oxygen and sulphur, OH, $OCH_3$, $OCH_2CH_3$, $OCHCH_3CH_3$, $OCH_2CHCH_3CH_3$, OPh, CCH, CCPh, CN, COOH, $NH_2$, CONHR' NHR' or NR'R" in which the R' and R" groups may be optionally a phenyl or a substituted phenyl, a 5 or 6 member azacyclic ring, $CH_3$, C1-C6 alkyl which optionally may incorporate one further heteroatom selected from oxygen, sulphur and nitrogen.

$R_{10}$ represents in compounds I to VI: H, $CH_3$, C1-C6 alkyl which optionally may incorporate one further heteroatom selected from nitrogen, oxygen and sulphur, a vinyl group of the general formula CH=CHR' in which the R' represents a H, $CH_3$, C1-C6 alkyl which optionally may incorporate one further heteroatom selected from oxygen, sulphur and nitrogen, a vinyl group of the general formula CH=CHAr in which the Ar represents optionally a phenyl, a substituted phenyl ring, a heteroaromatic ring comprising at least one ring heteroatom selected from nitrogen, oxygen and sulphur, an Ar in which the Ar group may be optionally a phenyl, a substituted phenyl ring, a Cl-, Br- or F-substituted phenyl ring in the o-, m- or p-positions, a naphthyl, a monocyclic or bicyclic heteroaromatic ring comprising at least one ring heteroatom selected from nitrogen, oxygen and sulphur.

$R_{11}$ represents in compounds III and VI: H, $CH_3$, C1-C6 alkyl which optionally may incorporate heteroatoms selected from nitrogen, oxygen and sulphur, a polyethylene glycol chain comprising azide, alkyne, alkene or maleimide derived functions, formyl or C2-C6 alkanoyl, amide, esters, $CH_2Ar$ or $CH_2CH_2Ar$ in which the Ar group may be optionally a phenyl, a substituted phenyl ring, a naphthyl, a heteroaromatic ring or fused ring comprising at least one ring heteroatom selected from nitrogen, oxygen and sulphur, OH, $OCH_3$, $OCH_2CH_3$, $OCHCH_3CH_3$, $OCH_2CHCH_3CH_3$, OPh, CCH, CCPh, CN, COOH, $NH_2$, CONHR' NHR' or NR'R" in which the R' and R" groups may be optionally a phenyl or a substituted phenyl, a 5 or 6 member azacyclic ring, $CH_3$, C1-C6 alkyl which optionally may incorporate one further heteroatom selected from oxygen, sulphur and nitrogen.

X and Y represent in compounds I to VI a heteroatom selected from oxygen or nitrogen.

Z represents in compounds III, IV and VI: A double bond with oxygen or nitrogen, or a simple bond with H, $CH_3$, C1-C6 alkyl which optionally may incorporate heteroatoms selected from nitrogen, oxygen and sulphur, a polyethylene glycol chain comprising azide, alkyne, alkene or maleimide derived functions, formyl or C2-C6 alkanoyl, $CH_2Ar$ or $CH_2CH_3Ar$ in which the Ar group may be optionally a phenyl, a substituted phenyl ring, a naphthyl, a heteroaromatic ring or fused ring comprising at least one ring heteroatom selected from nitrogen, oxygen and sulphur, OH, OCH$_3$, OCH$_2$CH$_3$, OCHCH$_3$CH$_3$, OCH$_2$CHCH$_3$CH$_3$, OPh, CCH, CCPh, CN, COOH, NH$_2$, CONHR' NHR' or NR'R" in which the R' and R" groups may be optionally a phenyl or a substituted phenyl, a 5 or 6 member azacyclic ring, CH$_3$, C1-C6 alkyl which optionally may incorporate one further heteroatom selected from oxygen, sulphur and nitrogen.

Preferred complexes are of any one of formulae (I), (II), (IV) and (V), more especially of formula (I). Alternatively, preferred complexes are of any one of formulae (I) to (V), such as (I), (IV) or (VI), or (I), (III) or (IV), more especially of formula (I).

Novel core complexes (i.e. excluding any of the components (a) to (d)) of the present invention include those of formula (II) or (V). Accordingly, the present invention further provides a novel complex of formula (II) or (V) as defined herein.

In any one of the core or multifunctional complexes disclosed herein, particularly preferred is wherein, when present, R1 is H, alkyl (e.g. CH3) or phenyl; R2 is H; R3 is H or a polyethylene glycol chain comprising azide, alkyne, alkene or maleimide functions; R4 is H or OCH3; R5 is H; R6 is H; R7 is H, an amide or a polyethylene glycol chain comprising azide, alkyne, alkene or maleimide functions; R8 and R9 are H; R10 is phenyl or a therapeutic cargo (e.g. an API such as Btz, SN38, chalcone or adamantylamine, or an imaging agent such as a coumarin derivative); and X, Y and Z are each O.

In any one of the formulae (I)-(VI), it is preferred that one or more of the following values apply:

R$_1$ is H, C$_{n=1\,1-6}$ alkyl (more preferably methyl) or phenyl;
R$_2$ is H;
R$_3$ is H, or is or includes the residue of a water-soluble moiety and/or a functionalising moiety and/or a targeting moiety, such as R$_x$-[—O—(—CH$_2$)$_2$-]$_3$—O— in which R$_x$ is a C$_{1-6}$ alkyl (e.g. methyl) chain optionally end-substituted by either an azide (N$_3$) group or a folate moiety such as a folate-cyclo-octyne derived from N2-(4-(((2-amino-4-oxo-3,4-dihydropteridin-6-yl)methyl)amino)benzoyl)-N5-(2-(((((1R,8S,9s)-bicyclo [6.1.0]non-4-yn-9y1)methoxy)carbonyl) amino)ethyl)-L-glutamine;
R$_4$ is H or C$_{n=1-6}$ alkoxy (more preferably methoxy);
R$_5$ and R$_6$ are H
R$_7$ is H, or is or includes the residue of a therapeutically useful cargo water-soluble moiety and/or a functionalising moiety and/or a targeting moiety, such as C$_{n=1-6}$ alkyl (e.g. where n=2) amide (e.g. —CO—NH—(CH$_2$)$_2$-) optionally incorporating a short chain PEG moiety (e.g. —CO—NH—(CH$_2$)$_2$-(OCH$_2$)$_3$-) terminating in either an azide (N$_3$) group or a folate moiety such as a folate-cyclo-octyne derived from N2-(4-(((2-amino-4-oxo-3,4-dihydropteridin-6-yl)methyl)amino)benzoyl)-N5-(2-(((((1R,8S,9s)-bicyclo[6.1.0]non-4-yn-9-yl)methoxy)carbonyl) amino)ethyl)-L- glutamine; or ((1R,8S,9s)-bicyclo[6.1.0]non-4-yn-9-yl)methyl(2-(2-(2-(2-(2,5-dioxo-2,5-dihydro-1H-pyrrol-1-yl)ethoxy)ethoxy)ethoxy)ethyl)carbamate, optionally itself terminating in a therapeutically useful cargo such as a residue of an API such as a peptide or a targeting unit such as a peptide such as RGD;
R$_8$ and R$_9$ are both H;
R$_{10}$ is phenyl, or the residue of a therapeutically useful cargo, such as a bioimaging molecule e.g. coumarin or a residue of an API (such as Btz, SN38, chalcone or adamantylamine);
R$_{11}$ (when present) is CH$_2$Ar in which the Ar group may be optionally phenyl, e.g. benzyl; and
X and/or Y and/or Z (when present) is O.

Preferably, any one or more of R$_1$ to R$_9$ (inclusive), R$_{11}$ and Z represent(s) a polyethylene glycol chain, optionally comprising one or more azide, alkyne, alkene or maleimide function(s) and/or represents C$_{n=1-6}$ alkyl, which incorporates more than one heteroatom(s) (N, O, S). The person skilled in the art will appreciate that there may be more than one way of defining particular substituents so that they fall within the definitions herein. For example, both the definitions of R$_3$ above {as R$_x$-[—O—(—CH$_2$)$_2$-]$_3$—O— in which R$_x$ is a C$_{n=1-6}$ alkyl chain optionally end-substituted by an azide (N$_3$) group} and of R$_7$ above {as C$_{n=1-6}$ alkyl amide (e.g. CO—NH—(CH$_2$)$_2$- or CO—NH—(CH$_2$)$_2$-(OCH$_2$)$_3$-) terminating in either an azide (N$_3$) group}, incorporate a polyethylene glycol chain comprising azide, alkyne, alkene or maleimide.

Suitably, any one or more of R$_2$ to R$_5$ (inclusive) and R$_{11}$ represent(s) an amide or ester group.

Preferably R$_2$ to R$_5$ (inclusive), R$_{11}$ and Z represent OH, OCH$_2$, OCH$_2$CH$_3$, OCHCH$_3$CH$_3$, OCH$_2$CHCH$_3$CH$_3$, OPh, CCH, CCPh, CN, COOH, NH$_2$, or CONHR', NHR' or NRR' in which the R' and R" groups may be optionally a phenyl or substituted phenyl, a 5 or 6 membered azacyclic ring, CH$_3$, or C$_{n=1-6}$ alkyl which optionally may incorporate one further heteroatom selected from O, S and N.

Preferably, when the core complex is of formula (III), it is other than wherein R$_4$ is diethylamine, R$_{10}$ is substituted phenyl, R$_{11}$ is phenyl, and X, Y and Z are each O, when all the remaining Rn groups are H.

Preferably, when the core complex is of formula (VI), it is other than wherein R$_{10}$ is H or phenyl, and X, Y and Z are each O, when all the remaining Rn groups are H.

Preferably, when the core complex is of formula (VI), it is other than either wherein R$_{11}$ is benzyl and/or wherein R$_{10}$ is substituted phenyl and R$_4$ is methyl, methoxy or diethylamine, and X, Y and Z are each O, when all the remaining Rn groups are H.

More preferably, R$_1$ is other than H; especially preferred is when R$_1$ is alkyl (such as methyl) or phenyl.

More preferably, R$_4$ is H or alkoxy (such as methoxy).

More preferably, R$_{10}$ is or comprises a residue of a therapeutic cargo or, especially when the therapeutic cargo is comprised in another Rn substituent (such as, post-functionalisation as described below, in R$_7$), R$_{10}$ is phenyl.

Especially preferred is when:
R$_1$ is methyl; R$_2$ is H;
R$_3$ is a polyethylene glycol chain comprising an azide function;
R$_7$ is an alkylamide comprising an azide function, preferably a CONH—(CH$_2$)$_2$ moiety comprising an azide function, and optionally a polyethylene glycol chain;
R$_2$, R$_4$, R$_5$, R$_6$, R$_8$ and R$_9$ each represent H; R$_{11}$ and Z are absent;
R$_{10}$ is a therapeutic cargo, such as a drug (API) or radio-imaging moiety, for example Btz or a coumarin derivative; and
X and Y each represent O.
Also preferred is when:
R$_1$ is phenyl;
R$_4$ is methoxy;
R$_{10}$ is a residue of a therapeutic cargo (such as a drug, for example, Btz, SN38, chalcone, adamantylamine) or is phenyl;
R$_2$, R$_3$, R$_5$-R$_9$ (inclusive) each represent H; R$_{11}$ and Z are absent; and
X and Y each represent O.

Alternatively, $R_1$ is preferably methyl, especially when $R_4$ is methoxy, and X, Y and Z (when present) are O and $R_{11}$ (when present) is phenyl. More preferred is when the structure is of formula (I).

When referred to herein, the polyethylene glycol (PEG) chain is preferably derived from a short chain PEG, more preferably of formula $[O-CH_2)_2]n$ wherein n is an integer from 3 to 6, especially 3.

Accordingly, the present invention further provides novel B-complex compounds of the following formulae, as described in the examples hereinbelow: 6, 7, 8, 9, 10, 11, 12, 13, 14, 15, 16, 17, 18, and 19 (wherein the peptide group is laminin, ovalbumin or RGD).

All the above definitions in relation to the complexes of the invention, including all combinations, preferences, alternatives, characteristics and the like, apply equally (unless the context indicates otherwise) throughout this specification to uses, compositions, processes, methods, products and the like, concerning the complexes or multifunctional conjugates comprising or derived therefrom.

The B-complex cores described above have the advantages that they can be assembled in one step, are stable in different biocompatible conditions, such as human plasma, physiological and intra-tumoural pH, but their assembly is reversible for example in the presence of a hydrolysing agent such as glutathione (GSH).

The present invention thereby enables the modular construction of multifunctional conjugates as described below, which are capable of exhibiting high selectivity towards, for example, folate-receptor-positive MDA-MB-231 cancer cells and an $IC_{50}$ in the low nanomolar range. The stimulus-responsive intracellular API delivery from the multi-functional boron complex of the invention can be confirmed by confocal fluorescence microscopy, and a mechanism for GSH-induced B-complex hydrolysis can be determined based on mass spectrometry.

Therefore, the tripodal boronated complexes (B-complexes), featuring reversible covalent bonds, were designed to accommodate, at least a drug, at least water-soluble moiety (e.g. polyethylene glycol (PEG) chains, cyclodextrins) and at least a targeting unit.

Accordingly, the invention further provides a multifunctional, tricomponent (tripodal) boronated complex (B-complex) having reversible covalent bonds enabling release of the functional components, according to any one of the foregoing formulae (I) to (VI), and comprising or further comprising: (a) at least one therapeutic cargo moiety (preferably an API); (b) at least one water-soluble moiety (e.g. polyethylene glycol (PEG) chains, cyclodextrins); and either or both of (c) at least one moiety capable of being post-functionalised with a targeting unit (d) and a targeting unit (preferably that targets a cancer cell).

The API suitably exhibits a boronic acid functionality, whereby a B-complex of the invention can be generated. Examples of suitable APIs include, but are not restricted to: anti-cancer (e.g. anti-breast, lung or melanoma cancer) drugs, such as Btz, SN38 or duocarmycin; anti-neurodegenerative (e.g. for treating Alzheimer's, Parkinson's or Huntington's) drugs, such as donepezil, memantine or levodopa; and anti-inflammatory (such as anti-rheumatoid arthritis) drugs, such as ibuprofen, prednisone or methotrexate. Btz is an especially suitable API because not only does it exhibit a boronic acid functionality but also it would benefit from improved selectivity through the targeting of cancer cells by the multifunctional construct.

Examples of water-soluble moieties include, but are not restricted to, polyethylene glycol (PEG) chains, sulphones, and cyclodextrins such as a beta-cyclodextrin or a modified beta-cyclodextrin. Such modified beta-cyclodextrin preferably comprises an inclusion complex of the cyclodextrin with another molecule, which can optionally be an active pharmaceutical ingredient (API), to improve the aqueous solubility of the active pharmaceutical ingredient. A preferred water-soluble moiety is a short chain PEG or derivative thereof as described hereinabove.

As explained above, the targeting unit is a moiety capable of targeting the site where the drug (API) binds or is active such that, on delivery of the multifunctional complex to the environment of the site, the drug (API) binds to the site or is activated at the site. Examples of targeting units include, but are not restricted to, small vitamins, peptides, proteins and enzyme inhibitors that recognize overexpressed receptors cells or diseased tissues. Preferred targeting units are selected from small vitamins (e.g. folic acid and derivatives thereof, and biotin), peptides (e.g. RGD, F3), proteins (e.g. albumin, herceptin, anti-CXCR4 antibody), enzyme inhibitors (e.g. CAIX inhibitors).

Folic acid is especially suitable as it is an essential vitamin for cell functioning and is commonly used as a recognition moiety because many cancer cell lines, due to their fast cell division and growth, overexpress receptors for this vitamin. The targeting unit is selected to improve potency of the API-delivering multifunctional complex in use; in particular, it ideally mediates internalization of the B-complex into cancer cells. Furthermore, a bi-folate recognition moiety may be incorporated into the complex to maintain the ability of the multifunctional complex to deliver an anticancer API such as Btz.

Especially preferred is a post-functionalised multi-functional complex in which any one of the multifunctional complexes previously described is further substituted by a moiety that enables or assists delivery or activation or effectiveness of the therapeutic cargo or is itself therapeutic cargo.

Accordingly, the present invention further comprises a post-functionalised multi-functional complex comprising a multifunctional complex as hereinbefore defined having a functionalising substituent (i.e. a moiety capable of being post-functionalised), such as an azide group (e.g. as shown in compounds 7, 9 and 11 in the following examples), wherein the functionalising substituent is substituted by the therapeutic cargo or by a targeting group, such as a folic acid derivative. Examples include wherein any azide group present in $R_3$ and/or $R_7$, as defined anywhere herein, is/are further substituted by a folate recognition moiety, such as by a cyclooctyne-folate derivative (e.g. as shown in compounds 8, 10 and 12 in the following examples).

The complexes as defined herein throughout including in the claims are to be taken to include salts, hydrates, and derivatives thereof (such as those known for use in the medicinal field), together with all isomers, (including stereoisomers, enantiomers, diastereomers), tautomers and forms (including crystal forms) thereof.

Preparation of Complexes

The B-complex cores of or for use in the invention can be prepared by methods known or analogous to those known to those skilled in the art, which comprise mixing together under reaction conditions at least three component compounds, which component compounds are adapted to covalently bond to form a complex having a core according to any one of formulae (I) to (VI) as defined above. An indication of such a method is given in FIG. 3 (in relation to examples A to D) below.

The reaction conditions optionally include a solvent such as water or an organic solvent such as an alkanol (e.g. ethanol), toluene, acetonitrile, DMSO, diethyl ether, or a combination of any of the foregoing. Preferably, the component compounds are admixed in equimolar amounts.

Preferably, one or more of the component compounds comprise(s) one or more of the components (a) to (c)/(d) of the finally desired multifunctional complexes of the invention. Suitably, such as for the preparation of a multifunctional complex based on core formula (I), (a) at least one API, preferably Btz; (b) at least one water-soluble moiety (e.g. a short-chain polyethylene glycol (PEG) residue or cyclodextrin- substituted 4-aminophenol); and (c) at least one moiety (e.g. an azide substituted o-aminophenol) capable of being post-functionalised with a targeting unit, are mixed together.

The reaction can be carried out at a temperature adapted to the components concerned and may be in the range of from −10 to 90° C. (with the lower ranges particularly suitable for post-functionalisation); for the complexes mentioned in the preceding paragraph, the reaction is preferably carried out at elevated temperature, for example, in the range of from 70-90° C. and for several hours, for example, in the range of from 10 to 36 h, preferably 18 to 24 h. Alternatively, milder conditions may be required as will be understood by the person skilled in the art. The reaction is preferably carried out in the presence of molecular sieves, for example wherein the sieve has a pore size in the nanometer range, such as 0.2-0.6 nm, preferably about 0.4 nm. Once complete, the reaction mixture can then be: (i) filtered and the retained solid washed (for example using water and/or an organic solvent such as hexane or ethanol; or (ii) filtered and purified via column or thin layer chromatography, using, as mobile phase, an organic solvent such as dichloromethane, ethyl acetate, a ketone such as butanone, or a combination of any of the foregoing), in each case, (i) or (ii), to yield the product B-complex.

For example, equimolar amounts of PEG-salicylketone, azido-aminophenol and Btz can be reacted together in dry acetonitrile at 75° C., over 18 h.

Figure 2:
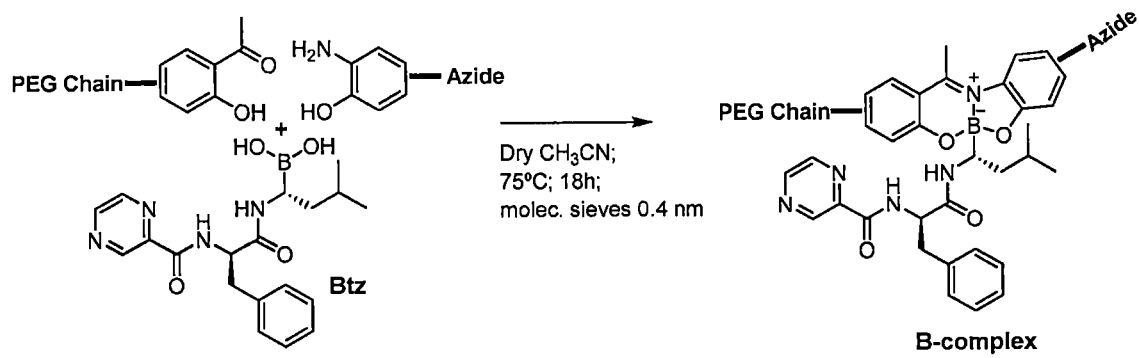
FIG. 2: General one-pot method to assemble a multifunctional B-complex.

Preferably, the method of assembling the B-complex is carried out in one step, as exemplified in FIG. 2. In this example, the functions of the components are as follows: PEG-salicylketone enhances water solubility; azido-aminophenol adds post click-functionalization with targeting units; and Btz is a potent anti-cancer drug.

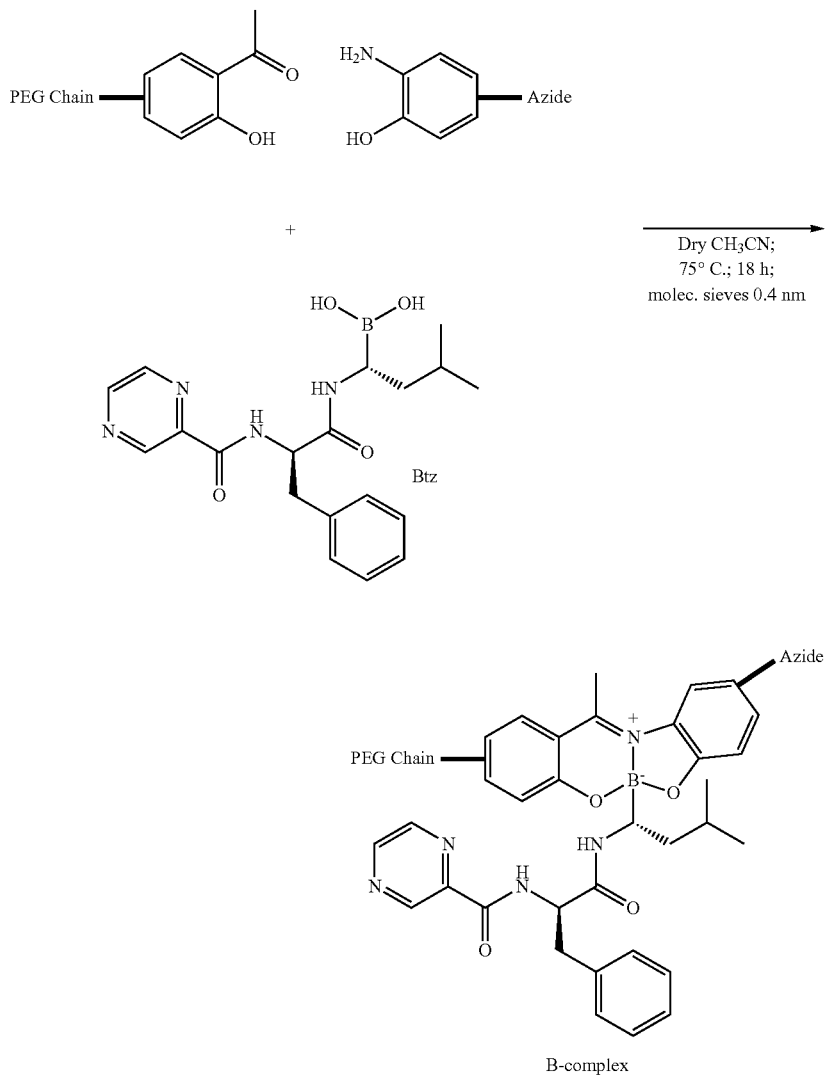

For example, to prepare a targeting multifunctional complex wherein the targeting moiety is a folate, a boronated core complex can be modified using hydroxyacetophenone and amino phenol, each substituted by small PEG chains terminating in a functional azide group, followed by post-functionalisation of the complex thereby formed with a folate-cyclo-octane component. Further details are given in the examples below, relating to compounds 7-10. Other examples are also provided.

Following the above schema and disclosure regarding structures of formula (I), it will be clear to a person skilled in the art how to adapt the starting component compounds for the preparation of other B-complex core structures.

Tests were carried out that proved that the B-complex core was stable in different biocompatible conditions, such as human plasma (e.g: $t_{1/2}$ (5)=39.6 h) at physiological pH (e.g: $t_{1/2}$(5)=39.8 h) or intratumoral pH (e.g: $t_{1/2}$(5)=38 h), though reversible in the presence of glutathione (GSH) (e.g: hydrolysis of 6 promoted by GSH lead to formation of Btz, which was detected by mass spectrometry m/z [M—OH]=367). The stimulus responsive intracellular cargo delivery was confirmed by confocal fluorescence microscopy and a mechanism for GSH induced B-complex hydrolysis was determined based on mass spectrometry. This platform thereby enables the modular construction of multivalent conjugates as described in FIG. 1, exhibiting high selectivity towards folate-receptor-positive MDA-MB-231 cancer cells and $IC_{50}$ in the low nanomolar range.

Pharmaceutical Uses and Compositions

In another aspect, the present invention provides the use of a complex of the invention in the preparation of a medicament (for therapy or prophylaxis) or diagnostic agent or prognostic agent. Alternatively or as well, the present invention provides a boronated compound of the invention or a pharmaceutically suitable salt or hydrate or derivative thereof for use in the preparation of a medicament for delivery of a therapeutically useful cargo, such as a drug or an API, to specific diseased tissue or cells.

Therefore, the present invention further provides a complex of the invention for use as a medicament, whether for therapy or prophylaxis, or as a diagnostic or prognostic agent. Alternatively or as well, the invention provides a boronated compound (B complex) of the invention or a pharmaceutically suitable salt thereof for use in a pharmaceutical composition, optionally in association with a pharmaceutically acceptable excipient, adjuvant, diluent and/or carrier.

Since it is envisaged that the complex and/or composition thereof is also for use as a diagnostic or prognostic agent, 'pharmaceutical' is taken to encompass such applications and not to be limited to therapy or prophylaxis.

Accordingly, in another aspect, the present invention provides a pharmaceutical composition comprising a complex of the invention together with a pharmaceutically acceptable carrier therefor. Alternatively or as well, the invention still further provides a pharmaceutical formulation comprising a boronated compound (B complex) of the invention in association with a pharmaceutically acceptable carrier therefor.

The pharmaceutically acceptable carrier may be any known in the art as suitable for such use and include solid or liquid excipients, diluents, lubricants, flowing agents and the like. Liquid forms for injection may comprise Water for Injections and/or saline as a main component of the carrier. They may also include flavouring or colouring agents, and optionally a coating or other enclosing materials such as, in the case of capsules, soft or hard gelatine.

Preferred pharmaceutical compositions are in the form of a solid dosage form, such as a tablet or capsule; or a liquid dosage form, such as a suspension or solution for oral or parenteral (e.g. intra-venous) use.

The pharmaceutical formulations of the invention may comprise in the range of from 0.1 to 100% of the complex of the invention by weight of the total formulation, depending on the particular components of the complex, the mode of use and the subject concerned. A single dose of the complex of the invention is determinable by methods known to those skilled in the art and will be effective for the use to which it is being put. For an adult human subject, the dose is optionally administered from one to six times daily or when required for diagnosis or prognosis, for example. However, these percentages and quantities are given only as a guide and the skilled pharmacologist, oncologist, pharmacist or other artisan will know how to calculate appropriate concentrations, dosages and dose regimes to fit particular circumstances of use.

Accordingly, the present invention moreover provides a complex or a pharmaceutical composition thereof for use in the treatment, prophylaxis, diagnosis or prognosis of a disease or condition preferably selected from neurodegeneration, inflammation and carcinogenesis in the treatment of diseases such as cancer (breast, melanoma or lung cancer), neurodegenerative diseases such Alzheimer, Parkinson and Huntington's and inflammatory diseases such rheumatoid arthritis.

Preferably, the complex or pharmaceutical composition thereof according to this invention is adapted to or is capable of releasing the therapeutic cargo in a subject at a site enabling a desired therapy, prophylaxis, diagnosis or prognosis. By 'in a subject' is generally meant in vivo, and the subject is preferably a human subject in need of the desired therapy, prophylaxis, diagnosis or prognosis.

These pharmaceutical compositions are used to deliver therapeutically useful cargo to specific diseased tissue or cells; and can be used in the manufacture of a medicament for the treatment of diseases or conditions in which targeted drug delivery is advantageous. In particular, the B complexes are useful to deliver therapeutically useful cargo to tissues that are for example in the process of neurodegeneration, inflammation and carcinogenesis in the treatment of diseases such as cancer (breast, melanoma or lung cancer), neurodegenerative diseases such Alzheimer, Parkinson and Huntington's and inflammatory diseases such rheumatoid arthritis.

Suitably, the therapeutic cargo is releasable on contact with a stimulus, ie a stimulus external to the complex or the composition in which it is comprised. More suitably, the external stimulus is selected from: enzymes, pH, GSH or another stimulus that results in a molecular rearrangement or breaking of covalent bonds in the complex, resulting in release of the cargo to the medium or environment in which it is comprised.

Preferably, the multifunctional complex of the invention has an 1050, determined as indicated in the examples, in the nanomolar range of from 1 to 100 nmoles, such as less than 50 and preferably less than 10 nmoles.

Accordingly, the present invention further provides a method for the treatment or prophylaxis of a disease or condition or for the diagnosis or prognosis of a disease or condition in a subject in need of such treatment, prophylaxis, prognosis or diagnosis, which method comprises administration to the subject of an effective amount of a multifunctional complex of this invention.

Conveniently, the complex or pharmaceutical composition thereof according to this invention is comprised in a suitable container therefore and, optionally, wherein the container itself is comprised in outer packaging. Optionally, the outer packaging further contains or includes instructions for use of the complex or pharmaceutical composition thereof The instructions for use may optionally include details of the desired therapy, prophylaxis, diagnosis or prognosis, dosage regime and dosage amount as indicated herein.

The following paragraphs illustrate further or alternative aspects of the invention disclosed herein:

A. Multifunctional compounds, incorporating in their structure boronated compounds (B complex) of the general formula (I to VI)

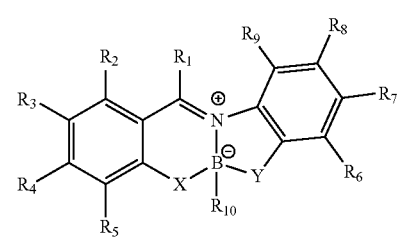
(I)

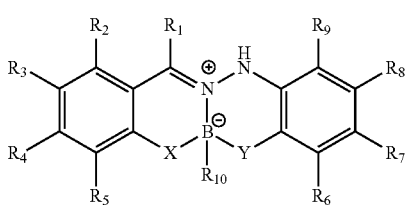
(II)

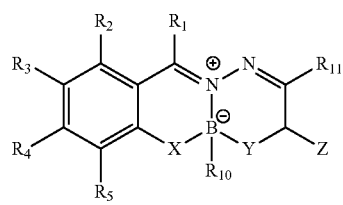
(III)

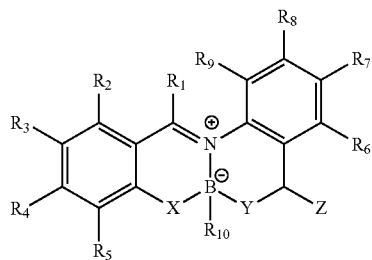
(IV)

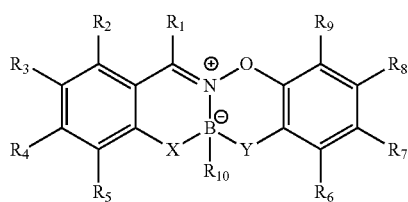
(V)

-continued

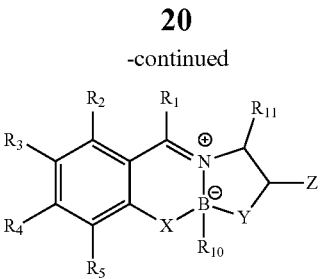
(VI)

B. Multifunctional compounds as described in paragraph A wherein at least one of the independent components is an active pharmaceutical ingredient.
C. Multifunctional compounds as described in paragraph A wherein the at least one active pharmaceutical ingredient is an anticancer (e.g. Btz, SN38 or duocarmycin) anti neurodegenerative (e.g. donepezil, memantine or levodopa) or antiinflamatory drug (e.g. ibuprofen, prednisone or methotrexate).
D. Multifunctional compounds as described in paragraph A wherein at least one of the independent components is a water soluble moiety.
E. Multifunctional compounds as described in paragraph D wherein the at least one water soluble moiety is a polyethylene glycol (PEG) or a cyclodextrin.
F. Multifunctional compounds as described in paragraph E wherein at least one water soluble molecule is a (3-cyclodextrin or a modified 3-cyclodextrin.
G. Multifunctional compounds as described in paragraph F wherein the modified 3-cyclodextrin is modified 3-cyclodextrin inclusion complex with another molecule.
H. Multifunctional compounds as described in paragraph G wherein the inclusion complex is a modified P-cyclodextrin inclusion complex with an active pharmaceutical ingredient.
I. Multifunctional compounds as described in paragraph A wherein at least one of the independent components is a targeting unit.
J. Multifunctional compounds as described in paragraph I wherein the at least the targeting unit is a small vitamins (e.g. folic acid, biotine), peptides (e.g. RGD, F3), proteins (e.g. albumin, herceptin, anti-CXCR4 antibody), enzyme inhibitors (e.g. CAIX inhibitors).
K. Method to assemble the B boronated compounds defined in paragraph A by mixing equimolar amounts of PEG-salicylketone, azidoaminophenol and Btz in dry acetonitrile at 75° C., over 18 hours.
L. Method to assemble the B boronated compounds defined in paragraph A comprising the use of a stimulus responsive protective group for biological active boronic acids with unfavourable pharmacokinetic and off-target toxicity.
M. Method according to paragraph L comprising the use of Schiff ligands as protective groups.
N. Method to assemble the B-complex core according to paragraph K wherein it is assembled in one step.
O. A method for making multifunctional compounds comprising the use of boronated compounds according to paragraph A.
P. Multifunctional compounds prepared according to the method of paragraph O with improved stability under biocompatible conditions such as physiological pH, intratumoral pH and plasma.

Q. Multifunctional compounds defined in paragraph A that, upon internalization on cancer cells, are able to undergo a stimulus responsive cargo delivery.

R. Multifunctional compounds defined in paragraph A that react with glutathione promoting the B-complex hydrolysis.

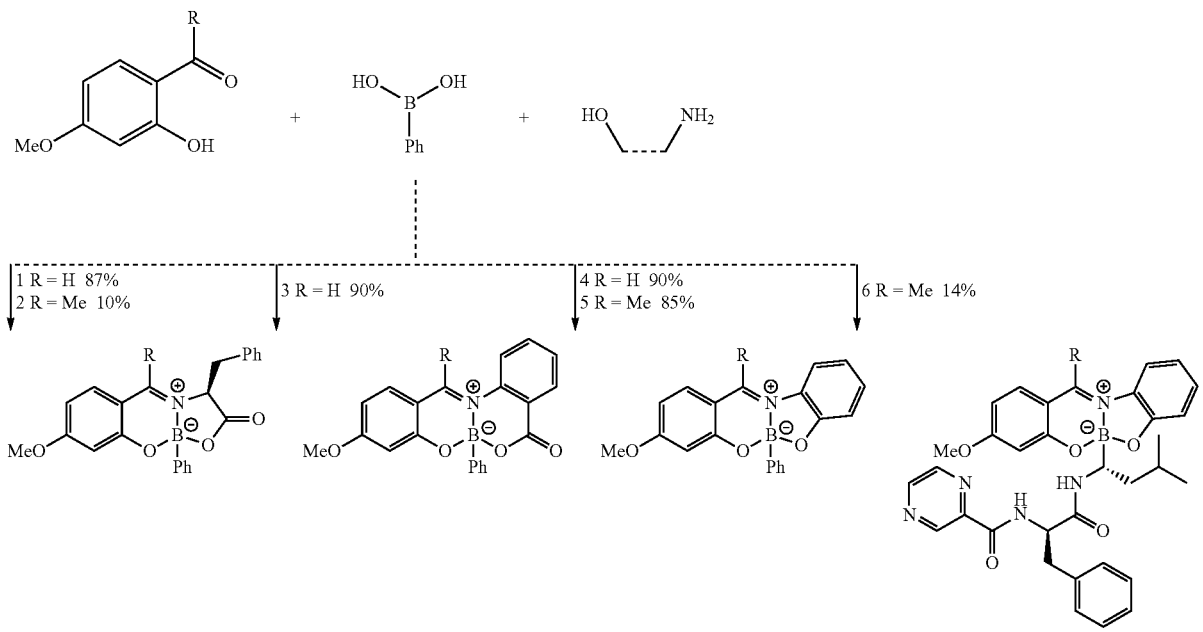

S. The use of boronated compounds according paragraph A to prepare multifunctional compounds.

T. A pharmaceutical composition comprising multifunctional compounds defined in paragraph A or a pharmaceutically suitable salt optionally with one or more pharmaceutically acceptable excipients.

U. A pharmaceutical composition comprising a boronated compound defined in paragraph A or a pharmaceutically suitable salt thereof in association with a pharmaceutically acceptable adjuvant, diluents and/or carriers.

V. Use of a boronated compound defined in paragraph A or a pharmaceutically suitable salt thereof or a pharmaceutical composition according to paragraph T, as a medicament W. Use according to paragraph V, to deliver therapeutic useful cargo to specific diseased tissue or cells.

X. Use according to paragraph V in the treatment of diseases or conditions in which targeted drug delivery is advantageous.

Y. Use according to paragraph U to deliver therapeutically useful cargo to tissues that are in the process of neurodegeneration, inflammation and carcinogenesis.

Z. Use according to paragraph U in the treatment of cancer neurodegenerative diseases and inflammatory diseases.

The present invention will now be illustrated with reference to the following examples, which shall not be taken to be limiting thereof. In particular, where an example illustrates mixing three (or more) components (a) to (c) as defined above, required to prepare the end-product (B core compound or multifunctional B complex, for example), the person skilled in the art will understand that any other combination of components, particularly those specified hereinbelow or hereinabove, can be substituted instead.

EXAMPLES

Figure 3:
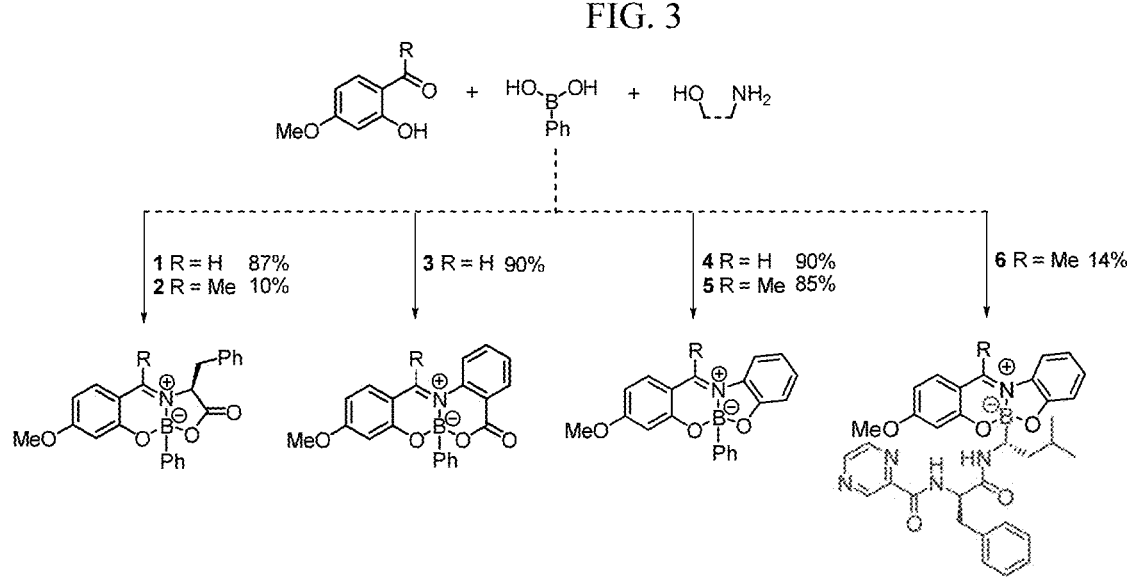
FIG. 3: Structure with reference to Examples A to D.

FIG. 3 is with reference to Examples A to D below:

Example A

Synthesis of B-Complexes 1 and 2

A round-bottomed flask was charged with 4-methoxysalicylaldehyde (Ex. A1) or 2-hydroxy-4-methoxyacetophenone (Ex. A2) (0.62 mmol), L-phenylalanine (0.82 mmol), and 2 mL of distilled water. This suspension was stirred at 90° C. for 1 h, after which the phenylboronic acid (0.41 mmol) was added. The mixture was then stirred at 90° C. for 20 h. The reaction mixture was filtered, and the solid retained in the filter was then washed with water (1 mL) followed by hexane (1 mL). B-complexes 1 and 2 were obtained as a white solid in 87% and 10% yield, respectively.

1—$^1$H NMR (400 MHz, CDCl$_3$) δ 7.50 7.42 (m, 2H, Arom), 7.36-7.28 (m, 6H, Arom), 7.04-6.93 (m, 4H, Arom), 6.49-6.46 (s, 1H, Imine CH), 6.44 (d, J=9.2 Hz, 1H, Arom), 4.27 (dd, J=12.0, 2.4 Hz, 1H, Arom), 3.82 (s, 3H, —OC$\underline{H}_3$), 3.36 (dd, J=12.0, 2.4 Hz, 1H, —C$\underline{H}_2$CH—), 2.67 (t, J=12.0 Hz, 1H, —C$\underline{H}_2$CH—); $^{13}$C NMR (101 MHz, CDCl$_3$) δ 170.99, 168.92, 162.79, 159.10, 135.60, 132.98, 130.86, 130.69, 129.56, 129.35, 129.20, 128.52, 128.41, 127.98, 127.90, 127.75, 111.61, 110.21, 102.75, 66.67, 55.97, 37.92; ESI: m/z ([M+H]$^+$): 386; E.A calcd (%) for C$_{23}$H$_{20}$BNO$_4$·¼H$_2$O: C70.88, H 5.3, N 3.59, found (%): C71.01, H 5.03, N 3.66. Half-life at pH 7.4=1.7 h.

2—$^1$H NMR (400 MHz, CDCl$_3$) δ 7.49-7.42 (m, 2H, Arom), 7.31-7.26 (m, 6H, Arom), 7.23 (d, J=9.2 Hz, 1H, Arom), 7.01-6.93 (m, 2H, Arom), 6.46 (dd, J=9.2, 2.4 Hz, 1H, Arom), 6.42 (d, J=2.4 Hz, 1H, Arom), 4.47 (dd, J=12.0, 3.2 Hz, 1H, —C$\underline{H}_2$CH—), 3.77 (s, 3H, —OC$\underline{H}_3$), 3.32 (dd, J=13.4, 3.2 Hz, 1H, —C$\underline{H}_2$CH—), 2.73 (dd, J=13.4, 12.0

Hz, 1H, —CH$_2$CH—), 1.52 (s, 3H, Imine CH$_3$); $^{13}$C NMR (101 MHz, CDCl$_3$) δ 171.72, 169.22, 167.57, 161.20, 136.42, 130.74, 130.30, 129.59, 129.31, 128.27, 127.91, 127.73, 112.94, 109.50, 102.97, 65.39, 55.78, 38.41, 16.72; ESI: m/z ([M+H]$^+$): 400; E.A calcd (%) for C$_{24}$H$_{22}$BNO$_4$·⅓H$_2$O: C 71.13, H 5.64, N 3.46, found (%): C71.46, H 5.88, N 3.25. Half-life at pH 7.4=32.2 h.

Example B

Synthesis of B-Complex 3

Equimolar amounts (0.3 mmol) of 4-methoxysalicylaldehyde, anthranilic acid and phenylboronic acid were added to a round bottomed flask and were dissolved in 2 mL of ethanol. This mixture was reacted at 70° C. for 18 h. Then, the reaction mixture was filtered and the solid obtained was washed with 1 mL of ethanol. B-complex 3 was obtained as a yellow solid in a 90% yield.

3—$^1$H NMR (400 MHz, DMSO) δ 9.42 (s, 1H, Imine CH), 8.05 (d, J=8.0 Hz, 1H, Arom), 8.01 (dd, J=7.6, 0.8 Hz, 1H, Arom), 7.82-7.75 (m, 1H, Arom), 7.70 (d, J=8.8 Hz, 1H, Arom), 7.53-7.47 (m, 1H, Arom), 7.19-7.12 (m, 2H, Arom), 7.12-7.06 (m, 3H, Arom), 6.68 (dd, J=8.8, 2.0 Hz, 1H, Arom), 6.59 (d, J=1.6 Hz, 1H, Arom), 3.87 (s, 3H, —OCH$_3$); $^{13}$C NMR (101 MHz, DMSO) δ 169.47, 161.54, 161.52, 159.41, 140.11, 135.61, 134.52, 130.56, 130.09, 128.56, 127.40, 123.27, 118.96, 110.45, 110.07, 101.57, 56.24; ESI: m/z ([M+H]$^+$): 358; E.A calcd (%) for C$_{21}$H$_{16}$BNO$_4$·H$_2$O: C67.23, H 4.84, N 3.73, found (%): C66.93, H 4.35, N 3.76. Half-life at pH 7.4=31.4 min. Half-life at pH 7.4=31.4 min.

Example C

Synthesis of B-Complexes 4 and 5

To a round-bottomed flask it were added equimolar amounts (0.3 mmol) of 4-methoxysalicylaldehyde (Ex. C4) or 2-hydroxy-4-methoxyaceto-phenone (Ex. C5), 2-aminophenol and phenylboronic acid. Then 2 mL of toluene was added and the mixture reacted at 80° C. for 18 h. B-complexes 4 and 5 were purified via filtration through a plug of silica, using dichloromethane as eluent. After evaporation of dichloromethane under reduced pressure, B-complexes 4 and 5 were obtained as a yellow solid in 90% and 85% yield, respectively.

4—Yellow solid; $^1$H NMR (400 MHz, CDCl$_3$): δ 8.22 (s, 1H, Imine CH), 7.42-7.32 (m, 3H, Arom), 7.32-7.24 (m, 2H, Arom), 7.21-7.12 (m, 3H, Arom), 7.08 (d, J=8.4 Hz, 1H, Arom), 6.88 (m, 1H, Arom), 6.67 (d, J=2 Hz, 1H, Arom), 6.52 (dd, J=8.4, 2 Hz, 1H, Arom), 3.87 (s, 3H, —OCH$_3$); $^{13}$C NMR (101 MHz, CDCl$_3$): δ 168.26, 160.49, 158.17, 148.07, 132.89, 131.34, 131.26, 127.86, 127.53, 119.26, 114.94, 114.54, 110.14, 102.98, 55.94; ESI: m/z ([M+Na]$^+$): 352; E.A calcd (%) for C$_{20}$H$_{16}$BNO$_3$: C72.98, H 4.9, N 4.26, found (%): C73.03, H 4.9, N 4.13. Half-life at pH 7.4=17.6 min.

5—Yellow solid; $^1$H NMR (400 MHz, CDCl$_3$): δ 7.54-7.40 (m, 2H, Arom), 7.35-7.23 (m, 3H, Arom), 7.16-7.07 (m, 4H, Arom), 6.87 (m, 1H, Arom), 6.70-6.65 (m, 1H, Arom), 6.52 (d, J=8.8 Hz, 1H, Arom), 3.87 (s, 3H, —OCH$_3$), 2.71 (s, 3H, Imine CH$_3$); $^{13}$C NMR (101 MHz, CDCl$_3$): δ 167.39, 160.67, 159.92, 158.92, 132.03, 131.36, 130.79, 130.32, 127.57, 127.40, 119.76, 118.67, 115.17, 114.70, 109.61, 103.07, 55.85, 18.18; ESI: m/z ([M+H]$^+$): 344; E.A calcd (%) for C$_{21}$H$_{18}$BNO$_3$: C73.5, H 5.29, N 4.08, found (%): C73.36, H 5.30, N 3.93. Half-life at pH 7.4=39.8 h, at pH 4.8=38 h and in human plasma=39.6 h.

Example D

Synthesis of B-Complex 6

A round-bottomed flask was flame-dried and maintained under argon with molecular sieves (0.4 nm). Equimolar amounts (0.2 mmol) of 2-hydroxy-4-methoxyacetophenone, 2-aminophenol and Btz were added to the flask and dissolved in 1.5 mL of dry acetonitrile. The reaction mixture was stirred for 18 h at 75° C. The molecular sieves were removed by filtration and then the acetonitrile was evaporated under reduced pressure. The crude mixture was dissolved in dichloromethane and purified via column chromatography using the following gradient: ethyl acetate 1:1 hexane:ethyl acetate. B-complex 6 was obtained as a yellow solid with 14% yield.

6—ESI: m/z ([M+H]$^+$): 606, ([M+Na]$^+$): 628, ([M+K]$^+$): 644; HMRS (ESI): m/z ([M+H]$^+$) calculated=606.28095, found m/z ([M+H]$^+$)=606.28597. Half-life in human plasma=60 h.

Examples A to D therefore illustrate B-complexes 1 to 6 and their preparation, based on a one-pot, three-component reaction in which 4-methoxysalicylaldehyde or acetophenone and boronic acids were reacted with L-phenyl alanine, anthranilic acid or 2-aminophenol. These complexes were used to evaluate the stability of the different iminoborate cores in several biomimetic media, as indicated by the half life data above. It can be seen that those core complexes wherein R1 is methyl have preferable stability compared to those wherein R1 is H.

Conjugate Disassembly Triggered by GSH

Further, GSH as a promoter of B-complex disassembly was evaluated in relation to compound 6 in plasma. Compound 6 was incubated with GSH in ammonium acetate buffer at pH 7.4 at 37° C., and the reaction was monitored by ESI-MS over 72 h. Analysis of the reaction mixture indicated the presence of an adduct combining the masses of compound 6 and GSH (m/z 912). Signals with m/z 367, 489 and 258 were also detected. Accordingly, the drug may (although we do not with to be bound by this theory) be released by addition of the GSH thiol group to the electrophicic imine carbon centre of compound 6 to to form an intermediate (m/z 912) present in the reaction mixture. This may destabilize the complex by increasing the electron density on the B atom, thus weakening the B—O bond of the aminophenol leading to opening of the 5-membered ring. Thereby, an intermediate is formed in which Btz (m/z 367) is more solvent-exposed, hence more susceptible to hydrolysis.

Example E

Synthesis of B-Complex 7

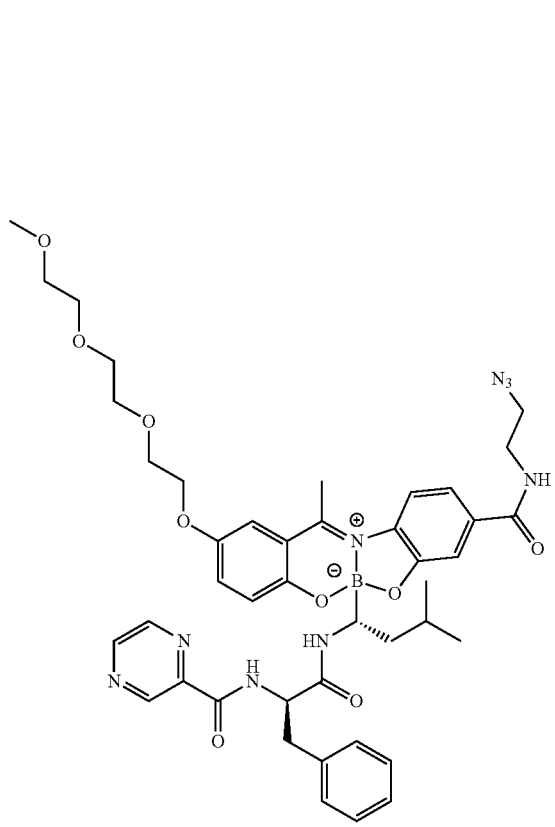

A round-bottomed flask was flame-dried and maintained under argon with molecular sieves (0.4 nm). Equimolar amounts (0.2 mmol) of PEG-acetophenone (i.e. 4-substituted acetophenone), azide-aminophenol and Btz were added to the round-bottomed flask and dissolved in 1.5 mL of dry acetonitrile. The reaction mixture was stirred for 18 h at 75° C. The molecular sieves were removed by filtration and then the acetonitrile was evaporated under reduced pressure. The crude mixture was dissolved in dichloromethane and purified via preparative TLC plate using butanone 3:1 hexane as eluent. B-complex 7 was obtained as a red/orange solid with 25% yield in a high degree of purity.

7—ESI: m/z ([M+H$^+$]): 850; HMRS (ESI): m/z ([M+H$^+$]) calculated=850.40874, found m/z ([M+H$^+$])=850.40401. MTS cell viability assay: IC$_{50}$ (MDA-MB-231)=non-cytotoxic at concentrations up to 100 nM; IC$_{50}$ (4T1)=0.67 mM.

Example E illustrates the synthesis and characterization of a multifunctional B-complex 7 based on the general structure (I), featuring Bortezomib (Btz) (R$_{10}$) as the API, a polyethylene glycol chain as the substituent R$_3$, and (R$_7$) an amide functionalized with an azide. It was evaluated in cytotoxic assays, as indicated by the IC$_{50}$ data above.

Example F

Synthesis of B-Complex 8

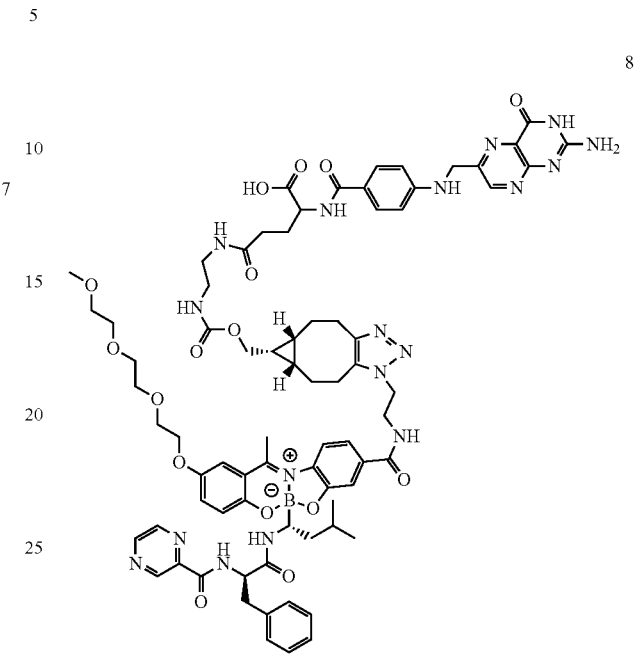

In a 2 mL test tube, a folate-cyclo-octyne {namely: N2-(4-(42-amino-4-oxo-3,4-dihydropteridin-6-yl)methyl)amino)benzoyl)-N5-(2-(((((1R,8S,9s)-bicyclo [6.1.0] non-4-yn-9-yl)methoxy)carbonyl)amino)ethyl)-L-glutamine; described in Org Biomol Chem. 2014 May 28; 12(20):3181-90} (6.63×10$^{-6}$ mol) and 7 (7.29×10$^{-6}$ mol) were dissolved in 650 µL of dry DMSO (reaction=10 mM). The mixture was placed in a temperature-controlled mixer (Thermomixer comfort™, Eppendorf) at 25° C., with 700 rpm for 17 h. Then, the reaction mixture was added dropwise into a mixture of 4 mL cold diethyl ether with 10% acetone. An orange precipitate, and the mixture was centrifuged (IKA mini G) for 1 minute. The supernatant was discarded, and the orange solid was then sequentially washed and centrifuged with 4 mL cold diethyl ether with 10% acetone, 4 mL cold acetone and 4 mL cold diethyl ether. B-complex 8 was obtained as an orange solid with 85% yield.

8—ESI: m/z ([M+2H]$^{2+}$): 756, ([M+H]$^+$): 1509; HMRS (ESI): m/z ([M+Na$^+$]) calculated=1531.66892, found m/z ([M+Na$^+$])=1531.70434. MTS cell viability assay: IC$_{50}$ (MDA-MB-231)=67.47 nM; IC$_{50}$ (4T1)=0.66 mM.

Example F: Illustrates the synthesis and characterization of a multifunctional B-complex (8) based on the general structure (I), featuring Bortezomib (R$_{10}$) as the API a polyethylene glycol chain as the substituent R$_3$, and (R$_7$) an amide functionalized with an azide that was further modified via a strain-promoted-azide-alkyne-cycloaddition with a folic acid unit that acts as the targeting component. It was evaluated in cytotoxic assays, as indicated by the MTS data provided above. Comparing data for compounds 7 and 8 demonstrate that the folate moiety confers cytotoxicity on the multifunctional complex.

Example G

Synthesis of B-Complex 9

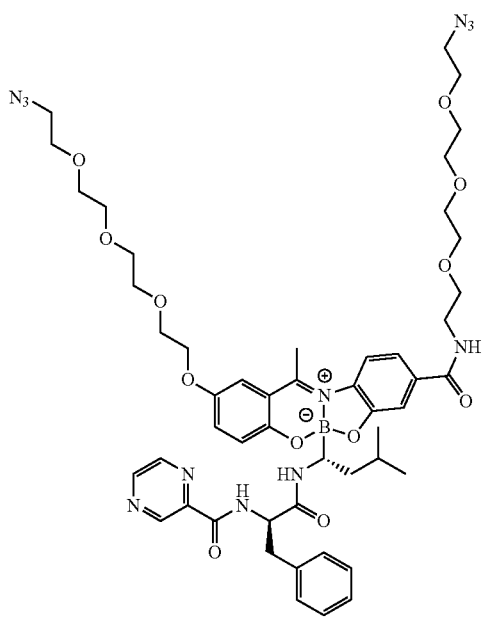

A round-bottomed flask was flame-dried and maintained under argon with molecular sieves (0.4 nm). Equimolar amounts (0.074 mmol) of azide-PEG-acetophenone, azide-PEG-aminophenol and Btz were added to the flask and dissolved in 1.5 mL of dry acetonitrile. The reaction mixture was stirred for 18 h at 75° C. The molecular sieves were removed by filtration and then the acetonitrile was evaporated under reduced pressure. The crude mixture was dissolved in dichloromethane and purified via preparative TLC plate using ethyl acetate as eluent. B-complex 9 was obtained as an orange solid with 8% yield.

9—HMRS (ESI): m/z ([M+H$^+$]) calculated=1037.50108, found m/z ([M+H$^+$])=1037.50683. MTS cell viability assay: IC$_{50}$ (MDA-MB-231)=non-cytotoxic at concentrations up to 100 nM; IC$_{50}$ (4T1)=7.25 mM.

Example G illustrates the synthesis and characterization of a multifunctional B-complex (9) based on the general structure (I), featuring Bortezomib (R$_{10}$) as the API, and a polyethylene glycol chain functionalized with a terminal azide as the substituents R$_3$ and R$_7$. It was evaluated in cytotoxic assays, as indicated by the MTS data provided above.

Example H

Synthesis of B-Complex 10

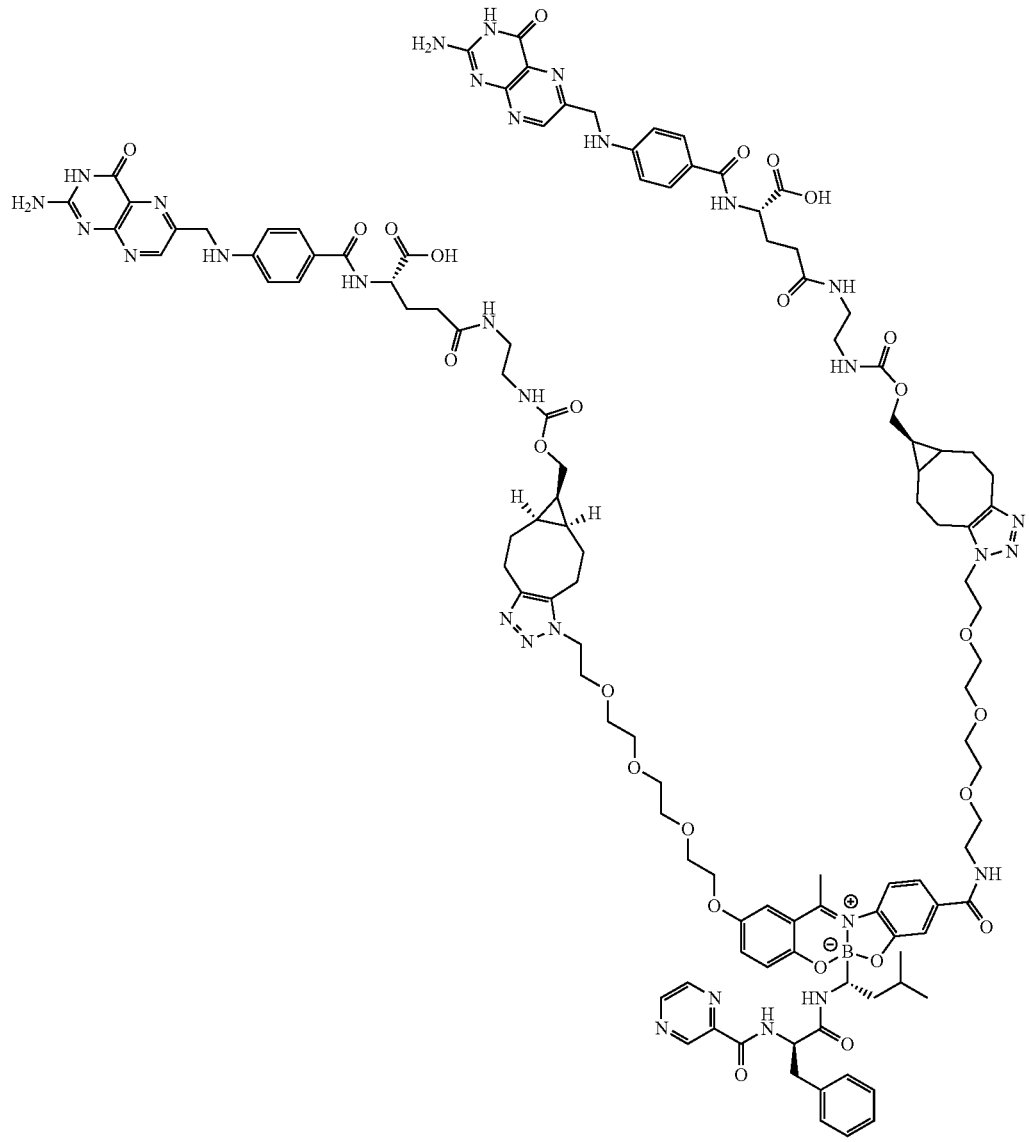

In a 2 mL Eppendorf, a folate-cyclooctyne {namely: N2-(4-(((2-amino-4-oxo-3,4-dihydropteridin-6-yl)methyl)amino)benzoyl)-N5-(2-(((((1R,8S,9s)-bicyclo[6.1.0]non-4-yn-9-yl)methoxy)carbonyl)amino)ethyl)-L-glutamine} ($4.1\times10^{-6}$ mol) and multi-functional B-complex according to Example G (9) ($2.05\times10^{-6}$ mol) were dissolved in 205 μL of dry DMSO ([ ]reaction=10 mM). The mixture was placed in a temperature-controlled mixer (Thermomixer comfort™, Eppendorf) at 25° C., with 700 rpm for 17 h. Then, the reactional mixture was dropwise into mixture of 1.5 mL of cold diethyl ether with 10% of acetone. An orange precipitate formal, and the mixture was centrifuged (IKA mini G) for 1 minute. The supernatant was discarded, and the orange solid was then sequentially washed and centrifuged with 1.5 mL cold diethyl ether with 10% of acetone, 1.5 mL cold acetone and 1.5 mL of cold diethyl ether. B-complex 10 was obtained as an orange solid with 99% yield.

10—HMRS (ESI): m/z ([M–$H_2O$]) calculated=2338.04699, found m/z ([M–$H_2O$])=2338.12592. MTS cell viability assay: $IC_{50}$ (MDA-MB-231)=62.02 nM; $IC_{50}$ (4T1)=0.59 mM.

Example H illustrates the synthesis and characterization of a multifunctional B-complex (10) based on the general structure (I), featuring Bortezomib ($R_{10}$) as the API, a polyethylene glycol chain functionalized with a terminal azide as the substituents in $R_3$ and $R_7$ that were further modified via a strain-promoted-azide-alkyne-cycloaddition with folic acid units that act as the targeting components. It was evaluated in cytotoxic assays, as indicated by the MTS data above.

Example I

Synthesis of B-Complex 11

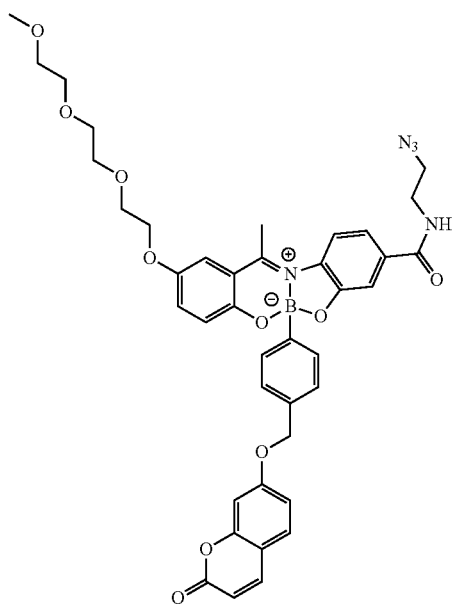

A round-bottomed flask was flame dried and maintained under argon with molecular sieves (0.4 nm). Equimolar amounts (0.053 mmol) of PEG-acetophenone and azide-aminophenol were added to the flask, and dissolved in 1.1 mL dry acetonitrile. A solution boronated coumarin (0.053 mmol) in 400L of dry DMF was added and the reactional mixture was stirred for 18 h at 75° C. Then, the molecular sieves were removed by filtration and the volatiles were evaporated. The crude mixture was dissolved in dichloromethane and purified via preparative TLC plate using butanone 2:1 hexane. B-complex 11 was obtained as a dark orange solid in a 17% yield.

11—$^1$H NMR (300 MHz, CDCl$_3$) δ 7.59 (d, J=9.7 Hz, 1H, —C$\underline{H}$=CH—), 7.54 (s, 1H, Arom), 7.42-7.28 (m, 4H, Arom), 7.25-7.20 (m, 3H, Arom), 7.18-7.11 (m, 3H, Arom), 7.07 7.02 (m, 1H, Arom), 6.85-6.75 (m, 2H, Arom), 6.58 (t, J=4.8 Hz, 1H, —N$\underline{H}$—), 6.21 (d, J=9.7 Hz, 1H, —CH=C$\underline{H}$—), 4.97 (s, 2H, —OC$\underline{H}_2$Ph-), 4.15-4.07 (m, 2H, Peg C$\underline{H}_2$), 3.91-3.80 (m, 2H, Peg C$\underline{H}_2$), 3.78-3.71 (m, 2H, Peg C$\underline{H}_2$), 3.71-3.60 (m, 6H, Peg C$\underline{H}_2$), 3.60-3.50 (m, 4H, —NHC$\underline{H}_2$C$\underline{H}_2$N$_3$), 3.37 (s, 3H, —OC$\underline{H}_3$), 2.79 (s, 3H, Imine C$\underline{H}_3$); $^{13}$C NMR (75 MHz, CDCl$_3$) δ 167.12, 162.99, 162.05, 161.45, 159.27, 155.79, 152.27, 151.72, 143.63, 136.89, 134.97, 134.11, 131.85, 128.82, 126.74, 121.54, 121.20, 120.29, 118.55, 113.34, 113.06, 112.71, 112.63, 112.57, 101.92, 71.99, 70.89, 70.72, 70.63, 69.85, 68.38, 59.14, 50.82, 39.66, 18.65; ESI: m/z ([M+H$^+$]): 762, ([M+Na$^+$]): 784; E.A calcd (%) for C$_{40}$H$_{40}$BN$_5$O$_{10}$·2H$_2$O: C 60.23, H 5.56, N 8.78, found (%): C 60.51, H 5.38, N 8.35.

Example I illustrates the synthesis and characterization a multifunctional B-complex (11) based on the general structure (I), featuring a non-fluorescent boronated coumarin (R$_{10}$), suitable for a bio-imaging application; a polyethylene glycol chain as the substituent R$_3$; and (R$_7$) an amide functionalized with an azide.

Example J

Synthesis of B-Complex 12

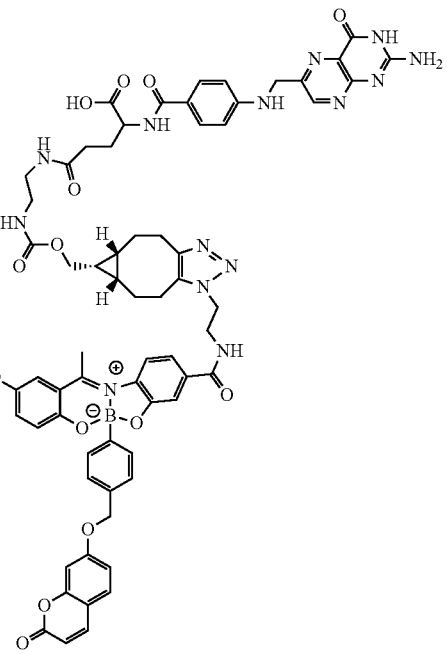

In a 1.5 mL test tube, a folate-cyclooctyne {namely: N2-(4-4(2-amino-4-oxo-3,4-dihydropteridin-6-yl)methyl) amino)benzoyl)-N5-(2-(((((1R,8S,9s)-bicyclo [6.1.0] non-4-yn-9-yl)methoxy)carbonyl)amino)ethyl)-L-glutamine} (1.2×10$^{-6}$ mol) and 11 (1.2×10$^{-6}$ mol) were dissolved in 120 µL of dry DMSO ([ ]reaction=10 mM). The mixture was placed in a temperature-controlled mixer (Thermomixer comfort™, Eppendorf) at 25° C., with 700 rpm for 17 h. Then, the reactional mixture was dropwise into mixture of 1 mL of cold diethyl ether with 10% of acetone. A dark brown precipitate formed, and the mixture was centrifuged (IKA mini G) for 1 minute. The supernatant was discarded, and the solid was then sequentially washed and centrifuged with 1 mL cold diethyl ether with 10% acetone, 1 mL cold acetone and 1 mL cold diethyl ether. B-complex 12 was obtained as a dark brown solid with 76% yield.

12—HMRS (ESI): m/z ([M+H$^+$]) calculated=1421.57569, found m/z ([M+H$^+$])=1421.57639.

Figure 4:
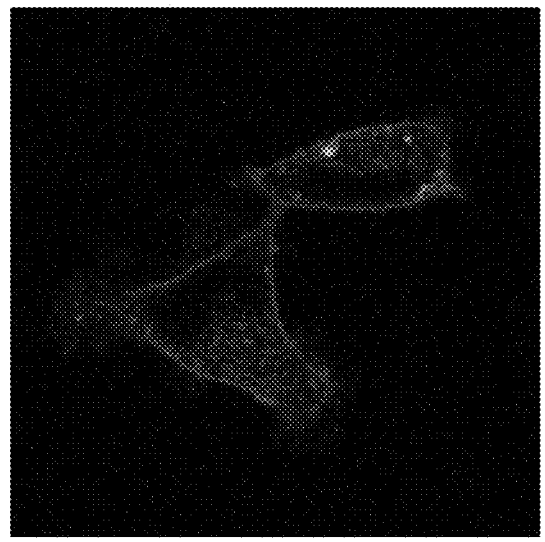
FIG. 4: Confocal fluorescence microscopy analysis of incubation of 12 in MDA-MB-231 human breast cancer cells. Plasma membrane was labelled with WGA-Alexa Fluor® 594.

Example J illustrates the synthesis and characterization of a multifunctional B-complex (12) based on the general structure (I), featuring a non-fluorescent boronated coumarin (R$_{10}$) suitable for a bio-imaging application; a polyethylene glycol chain as the substituent R$_3$; and (R$_7$), an amide functionalized with an azide that was further modified via a strain-promoted-azide-alkyne-cycloaddition with a folic acid unit that acts as the targeting component. It was used to confirm the intracellular cargo/API delivery via confocal fluorescence microscopy in MDA-MB-231 human breast cancer cells. The plasma membrane was labelled with WGA-Alexa Fluor® 594. The result is shown in FIG. 4.

Example K

Syntheses of B-complexes 13-16

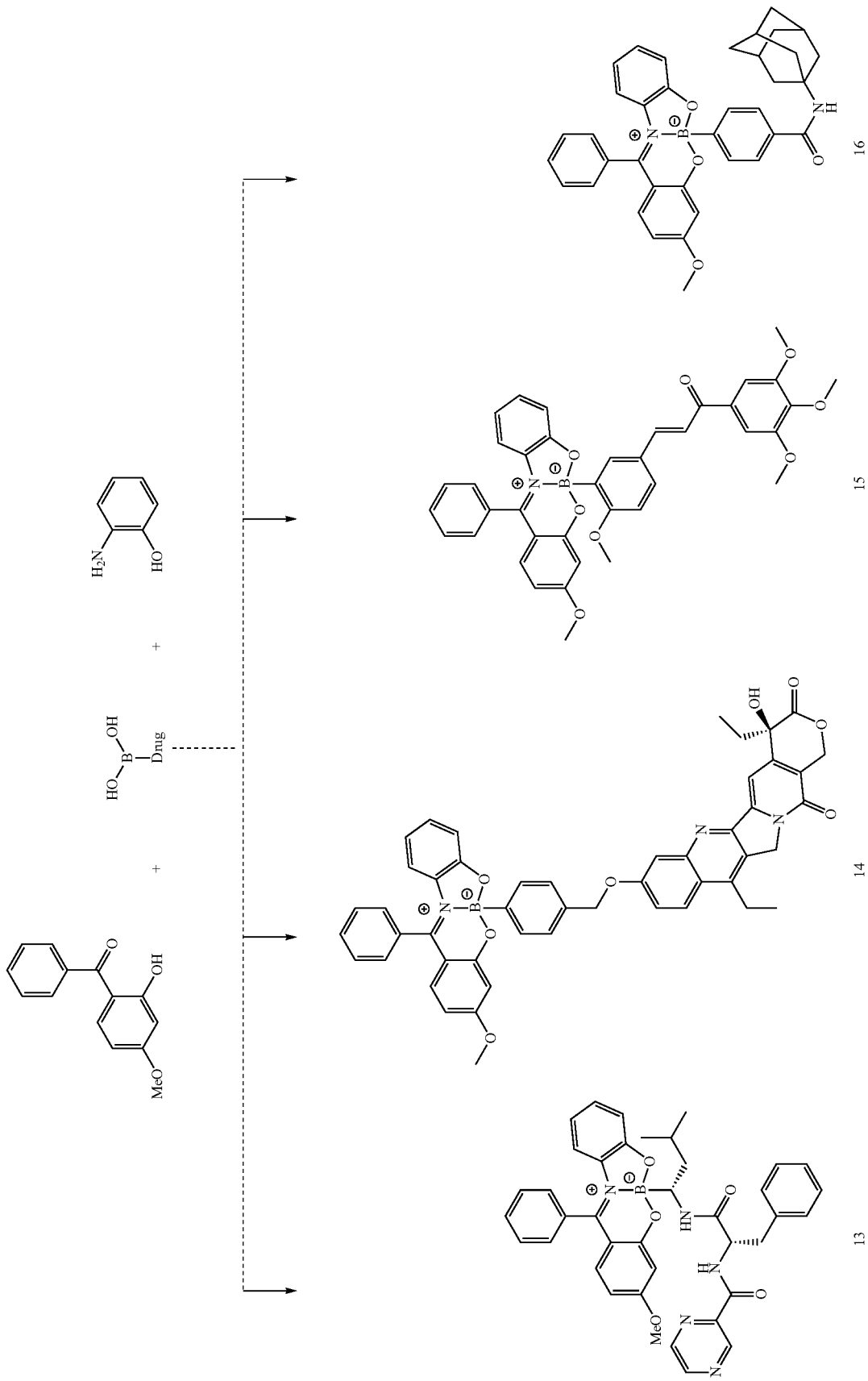

A round-bottomed flask was charged with equimolar amounts (0.1 mmol) of 2-hydroxy-4-methoxybenzophenone, 2-aminophenol, a boronated API (drug) derivatives (respectively, Btz, SN38, chalcone and adamantyl amine) and 1.5 mL of acetonitrile. The reaction mixtures were set at 80° C. for 18 h. Formation of compounds 13-16 was confirmed via LMRS (ESI).

13—LMRS (ESI): m/z ([M+H$^+$]) calculated=668, found m/z ([M+H$^+$])=668.

14—LMRS (ESI): m/z ([M+H$^+$]) calculated=810, found m/z ([M+H$^+$])=810.

15—LMRS (ESI): m/z ([M+H$^+$]) calculated=656, found m/z ([M+H$^+$])=656.

16—LMRS (ESI): m/z ([M+H$^+$]) calculated=583, found m/z ([M+H$^+$])=583.

Example K illustrates the synthesis of B-complexes 13-16 based on the general structure (I), featuring several different boronated drug or API derivatives (Btz, SN38, chalcone and adamantyl amine, respectively) (R$_{10}$) for use in the treatment of different diseases, such as cancer and Parkinson's disease, in accordance with the known indication(s) for each drug or API.

Example L

Synthesis of B-Complex 17 and Post-Functionalization with Peptides

A

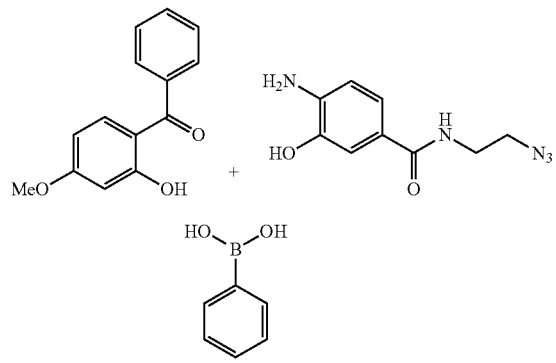

B

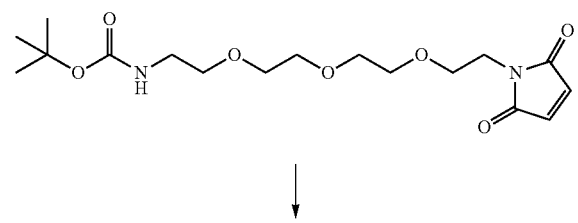

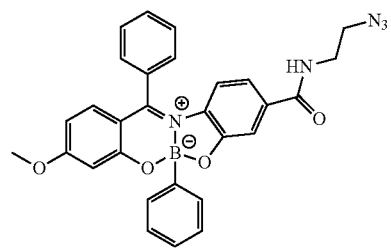

17

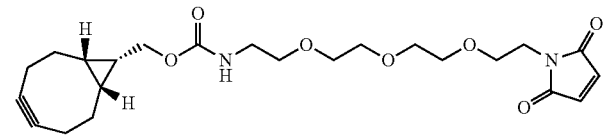

C

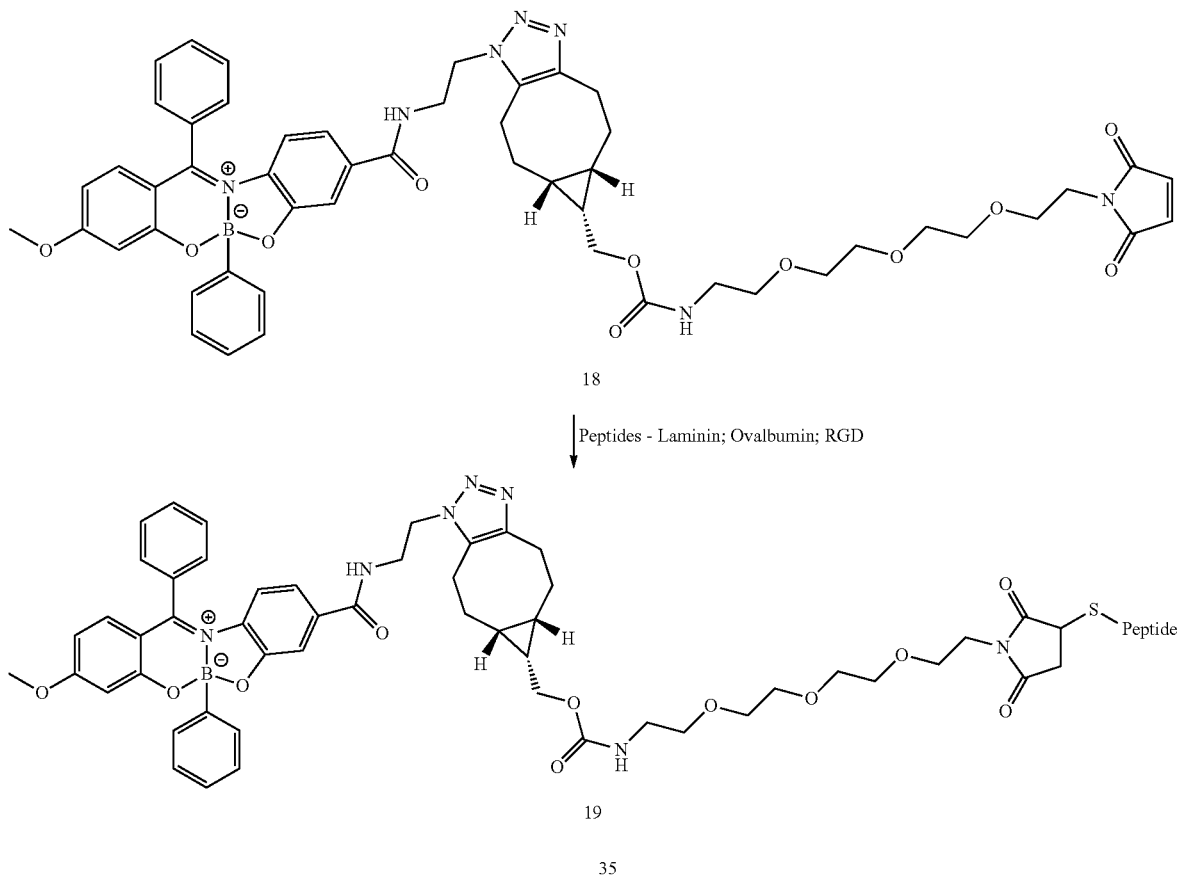

Reaction A: A round-bottomed flask was charged with equimolar amounts (0.1 mmol) of 2-hydroxy-4-methoxybenzophenone, 2-aminophenol azide derivative, phenylboronic acid and 1.5 mL of acetonitrile. The reaction mixture was stirred at 80° C. for 18 h. After that, acetonitrile was evaporated under reduced pressure, and the crude mixture was dissolved in dichloromethane and purified via preparative TLC plate using ethyl acetate 1:1 hexane as eluent. B-complex 17 was obtained as a yellow solid and confirmed by LMRS (ESI) m/z ([M+H$^+$]) calculated=518, found m/z ([M+H$^+$])=518.

Reaction B: In a round-bottomed flask, tert-butyl (2-(2-(2-(2-(2,5-dioxo-2,5-dihydro-1H-pyrrol-1-yl)ethoxy)ethoxy)ethoxy)ethyl)carbamate (0.269 mmol) was dissolved in a 2 mL mixture of TFA 1:1 dichloromethane and stirred for 30 min. Then, the volatiles were evaporated under reduce pressure and the crude mixture was redissolved in 2 ml of dichloromethane. To this solution it was added DIPEA (1.61 mmol) and (1R,8S,9s)-bicyclo[6.1.0]non-4-yn-9-ylmethyl N-succinimidyl carbonate. The mixture was stirred for 18 h. Then the volatiles were evaporated and the desired product, ((1R,8S,9s)-bicyclo[6.1.0]non-4-yn-9-yl)methyl(2-(2-(2-(2-(2,5-dioxo-2,5-dihydro-1H-pyrrol-1-yl)ethoxy)ethoxy)ethoxy)ethyl)carbamate, was obtained after thin layer chromatography using ethyl acetate 3:1 hexane as mobile phase. LMRS (ESI) m/z ([M+Na$^+$]) calculated=471, found m/z ([M+Na$^+$])=471.

Reaction C: In a 1.5 mL test tube, ((1R,8S,9s)-bicyclo[6.1.0]non-4-yn-9-yl)methyl (2-(2-(2-(2-(2,5-dioxo-2,5-dihydro-1H-pyrrol-1-yl)ethoxy)ethoxy)ethoxy)ethyl)carbamate and 17 were dissolved in acetonitrile ([reaction]=10 mM). The mixture was placed in a temperature-controlled mixer (Thermomixer comfort™, Eppendorf) at 25° C., 700 rpm for 17 h. Meanwhile, to a different solutions of peptide (Laminin (GeneCust, P170423_1), ovalbumin (Aldrich) or RGD (arginylglycylaspartic acid, GeneCust, P160388), respectively) (5×10$^{-9}$ mol) in 0.5 mL of acetate buffer 20 mM, pH 7.0, with 1% DMF, was added a solution of Tris(2-carboxyethyl)phosphine hydrochloride (1.5×10$^{-8}$ mol) in water. The reaction mixture was mixed in a temperature-controlled mixer (Thermomixer comfort™, Eppendorf) for 2 h at 25° C. Then, was added 5 μL from 18. The reaction mixture was stirred in the mixer for 1 h at 25° C., and formation of compounds 19 were confirmed via LMRS (ESI).

19 (Peptide=laminin)—LMRS (ESI): m/z ([M+2H]$^{2+}$) calculated=967, found m/z ([M+2H]$^{2+}$)=967.

19 (Peptide=ovalbumin)—LMRS (ESI): m/z ([M+2H]$^{2+}$) calculated=1017, found m/z ([M+2H]$^{2+}$)=1017.

19 (Peptide=RGD) LMRS (ESI): m/z ([M+3H]$^{3+}$) calculated=582, found m/z ([M+3H]$^{3+}$)=582.

Example L illustrates the synthesis of B-complex 17 based on the general structure (I), featuring (R$_7$) an amide functionalized with an azide that was further modified (via a strain-promoted-azide-alkyne-cycloaddition) with a maleimide handle, being a moiety capable of being post-functionalized, giving rise to B-complex 18. This complex 18 is based on the general structure (I), featuring (R$_7$) an amide functionalized with an maleimide for cysteine bio-conjugation with a peptide (in this case, chosen from laminin, ovalbumin and RGD) to construct B-complexes 19. These complexes 19 are based on the general structure (I), featuring ($R_7$) an amide functionalized with different peptides, respectively, as indicated above.

The invention claimed is:
1. A multifunctional compound comprising a tripodal boranated core, wherein the multifunctional compound further comprises:
    (a) at least one therapeutically useful cargo molecule, or a residue thereof;
    (b) at least one water-soluble moiety or a residue of a water-soluble molecule; and at least one of components (c) or (d), wherein
    (c) is at least one functionalizing moiety capable of being post-functionalised with a targeting unit or a residue of a targeting molecule; and
    (d) is at least one targeting unit or a residue of a targeting molecule;
    in which any residue of a molecule is such that, on breaking at least one covalent bond of the multifunctional compound, the complete molecule is released; and
wherein the tripodal boronated core is as defined in the general formula:

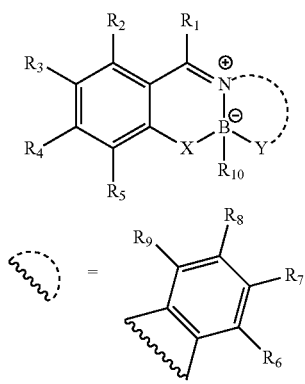

wherein:
$R_1$ represents H, $C_{n=1-6}$ alkyl, alkene or alkyne which can be straight, branched or cyclic and optionally contain one or more heteroatoms selected from nitrogen, oxygen or sulphur; formyl or $C_{n=2-6}$ alkanoyl; or Ar, $CH_2Ar$ or $CH_2CH_2Ar$, in which the Ar group may be a phenyl, a Cl-, Br- or F- substituted phenyl ring in the o-, m- or p- positions, a naphthyl, a heterocyclic ring or fused ring comprising at least one ring heteroatom selected from nitrogen, oxygen or sulphur;
$R_2$ to $R_5$ represents H, $C_{n=1-6}$ alkyl, alkene or alkyne which can be straight, branched or cyclic and optionally contain one or more heteroatoms selected from nitrogen, oxygen or sulphur; formyl or $C_{n=2-6}$ alkanoyl; amide; ester; Ar, $CH_2Ar$ or $CH_2CH_2Ar$ in which the Ar group may be a phenyl, a Cl-, Br- or F- substituted phenyl ring in the o-, m- or p- positions, a naphthyl, a heterocyclic ring or fused ring comprising at least one ring heteroatom selected from nitrogen, oxygen or sulphur, OH, $OCH_3$, $OCH_2CH_3$, $OCHCH_3CH_3$, $OCH_2CHCH_3CH_3$, OPh, CCH, CCPh, CN, COOH, $NH_2$, CONHR' NHR' or NR'R" in which the R' and R" groups may be optionally a phenyl, a substituted phenyl, a 5 or 6 member azacyclic ring, $C_{n=1-6}$ alkyl which optionally may incorporate one further heteroatom selected from oxygen, sulphur or nitrogen;
$R_6$ to $R_9$ represents H, $C_{n=1-6}$ alkyl, alkene or alkyne which can be straight, branched or cyclic and optionally contain one or more heteroatoms selected from nitrogen, oxygen or sulphur; formyl or $C_{n=2-6}$ alkanoyl; amide; ester; Ar, $CH_2Ar$ or $CH_2CH_2Ar$ in which the Ar group may be a phenyl, a Cl-, Br- or F- substituted phenyl ring in the o-, m- or p- positions, a naphthyl, a heterocyclic ring or fused ring comprising at least one ring heteroatom selected from nitrogen, oxygen or sulphur, OH, $OCH_3$, $OCH_2CH_3$, $OCHCH_3CH_3$, $OCH_2CHCH_3CH_3$, OPh, CCH, CCPh, CN, COOH, $NH_2$, CONHR' NHR' or NR'R" in which the R' and R" groups may be optionally a phenyl, a Cl-, Br- or F- substituted phenyl ring in the o-, m- or p- positions, a 5 or 6 member azacyclic ring, $C_{n=1-6}$ alkyl which optionally may incorporate one further heteroatom selected from oxygen, sulphur or nitrogen;
$R_{10}$ represents H, $C_{n=1-6}$ alkyl, alkene or alkyne which can be straight, branched or cyclic and optionally contain one or more heteroatoms selected from nitrogen, oxygen or sulphur; a vinyl group of the general formula CH=CHR' in which the R' represents a H, $C_{n=1-6}$ alkyl, alkene or alkyne which can be straight, branched or cyclic and optionally contain one or more heteroatom selected from nitrogen, oxygen or sulphur, a phenyl or a Cl-, Br- or F- substituted phenyl ring in the o-, m- or p-positions, a naphthyl, a monocyclic or bicyclic heterocyclic ring comprising at least one ring heteroatom selected from nitrogen, oxygen or sulphur; a phenyl or a Cl-, Br- or F- substituted phenyl ring in the o-, m- or p- positions; a naphthyl; or a monocyclic or bicyclic heterocyclic ring comprising at least one ring heteroatom selected from nitrogen, oxygen or sulphur; and
X and Y each independently represent a heteroatom selected from oxygen or nitrogen
wherein the at least one therapeutically useful cargo molecule, or a residue thereof comprises an API selected from anti-cancer agents; anti-neurodegeneratives; or anti-inflammatories; and/or an agent selected from chalcone, adamantylamine, or peptides.
2. The multifunctional compound as claimed in claim 1, wherein the tripodal boronated core is as defined in claim 1;
$R_1$ represents: H, $CH_3$, $C_1$-$C_6$ alkyl which optionally may incorporate heteroatoms selected from nitrogen, oxygen or sulphur, a polyethylene glycol chain comprising azide, alkyne, alkene or maleimide derived functions, formyl or $C_2$-$C_6$ alkanoyl, $CH_2Ar$ or $CH_2CH_2Ar$ in which the Ar group may be a phenyl, a substituted phenyl ring, a naphthyl, a heteroaromatic ring or fused ring comprising at least one ring heteroatom selected from nitrogen, oxygen or sulphur;
$R_2$ to $R_5$ represents: H, $CH_3$, $C_1$-$C_6$ alkyl which optionally may incorporate heteroatoms selected from nitrogen, oxygen or sulphur, a polyethylene glycol chain comprising azide, alkyne, alkene or maleimide derived functions, formyl or $C_2$-$C_6$ alkanoyl, amide, esters, $CH_2Ar$ or $CH_2CH_2Ar$ in which the Ar group may be a phenyl, a substituted phenyl ring, a naphthyl, a heteroaromatic ring or fused ring comprising at least one ring heteroatom selected from nitrogen, oxygen or sulphur, OH, $OCH_3$, $OCH_2CH_3$, $OCHCH_3CH_3$, $OCH_2CHCH_3CH_3$, OPh, CCH, CCPh, CN, COOH, $NH_2$, CONHR' NHR' or NR'R" in which the R' and R" groups may be optionally a phenyl or a substituted phenyl, a 5 or 6 member azacyclic ring, $CH_3$, $C_1$-$C_6$ alkyl which optionally may incorporate one further heteroatom selected from oxygen, sulphur or nitrogen;

$R_6$ to $R_9$ represents: H, $CH_3$, $C_1$-$C_6$ alkyl which optionally may incorporate heteroatoms selected from nitrogen, oxygen or sulphur, a polyethylene glycol chain comprising azide, alkyne, alkene or maleimide derived functions, formyl or $C_2$-$C_6$ alkanoyl, amide, esters, $CH_2Ar$ or $CH_2CH_2Ar$ in which the Ar group may be a phenyl, a substituted phenyl ring, a naphthyl, a heteroaromatic ring or fused ring comprising at least one ring heteroatom selected from nitrogen, oxygen or sulphur, OH, $OCH_3$, $OCH_2CH_3$, $OCHCH_3CH_3$, $OCH_2CHCH_3CH_3$, OPh, CCH, CCPh, CN, COOH, $NH_2$, CONHR' NHR' or NR'R" in which the R' and R" groups may be optionally a phenyl or a substituted phenyl, a 5 or 6 member azacyclic ring, $CH_3$, $C_1$-$C_6$ alkyl which optionally may incorporate one further heteroatom selected from oxygen, sulphur or nitrogen;

$R_{10}$ represents: H, $CH_3$, $C_1$-$C_6$ alkyl which optionally may incorporate one further heteroatom selected from nitrogen, oxygen or sulphur, a vinyl group of the general formula CH=CHR' in which the R' represents a H, $CH_3$, $C_1$-$C_6$ alkyl which optionally may incorporate one further heteroatom selected from oxygen, sulphur or nitrogen, a vinyl group of the general formula CH=CHAr in which the Ar represents a phenyl, a substituted phenyl ring, a heteroaromatic ring comprising at least one ring heteroatom selected from nitrogen, oxygen or sulphur, an Ar in which the Ar group may be a phenyl, a substituted phenyl ring, a Cl-, Br- or F- substituted phenyl ring in the o-, m- or p- positions, a naphthyl, a monocyclic or bicyclic heteroaromatic ring comprising at least one ring heteroatom selected from nitrogen, oxygen or sulphur; and X and Y represent a heteroatom selected from oxygen or nitrogen.

3. The multifunctional compound according to claim 1, wherein: $R_1$ is H, $C_{n=1-6}$ alkyl or phenyl;

$R_2$ is H;

$R_3$ is H, or is or includes the residue of a water-soluble moiety and/or a functionalising moiety and/or a targeting moiety;

$R_4$ is H or alkoxy;

$R_5$ and $R_6$ are H;

$R_7$ is H, or is or includes the residue of a therapeutically useful cargo water-soluble moiety and/or a functionalising moiety and/or a targeting moiety;

$R_8$ and $R_9$ are both H;

$R_{10}$ is phenyl, or the residue of a therapeutically useful cargo or a residue of an API; and X and/or Y is O.

4. The multifunctional compound as claimed in claim 1, wherein the water-soluble moiety is selected from polyethylene glycol (PEG) derivatives, sulphones or cyclodextrins.

5. The multifunctional compound as claimed in claim 1, wherein the targeting unit is a moiety capable of targeting the site where an API binds or is active.

6. The multifunctional compound as claimed in claim 1, wherein the functionalising moiety is an azide group.

7. The multifunctional compound as claimed in claim 1, selected from any of compounds 6 to 19:

6

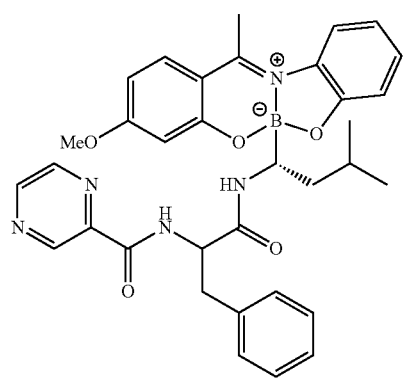

7

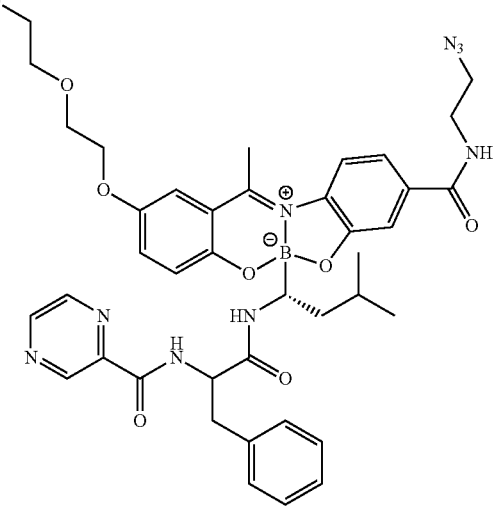

-continued
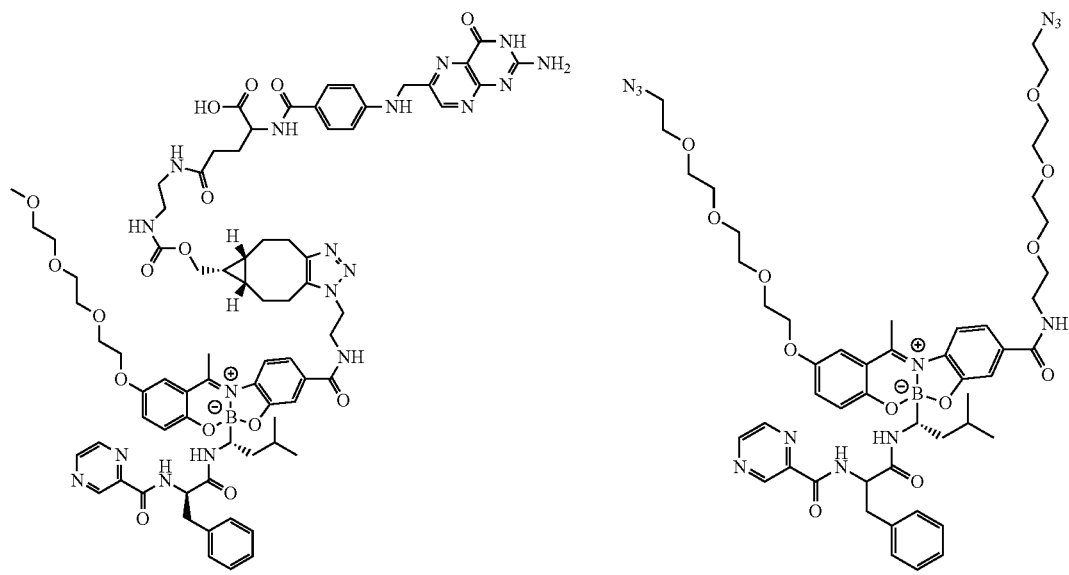
8
9
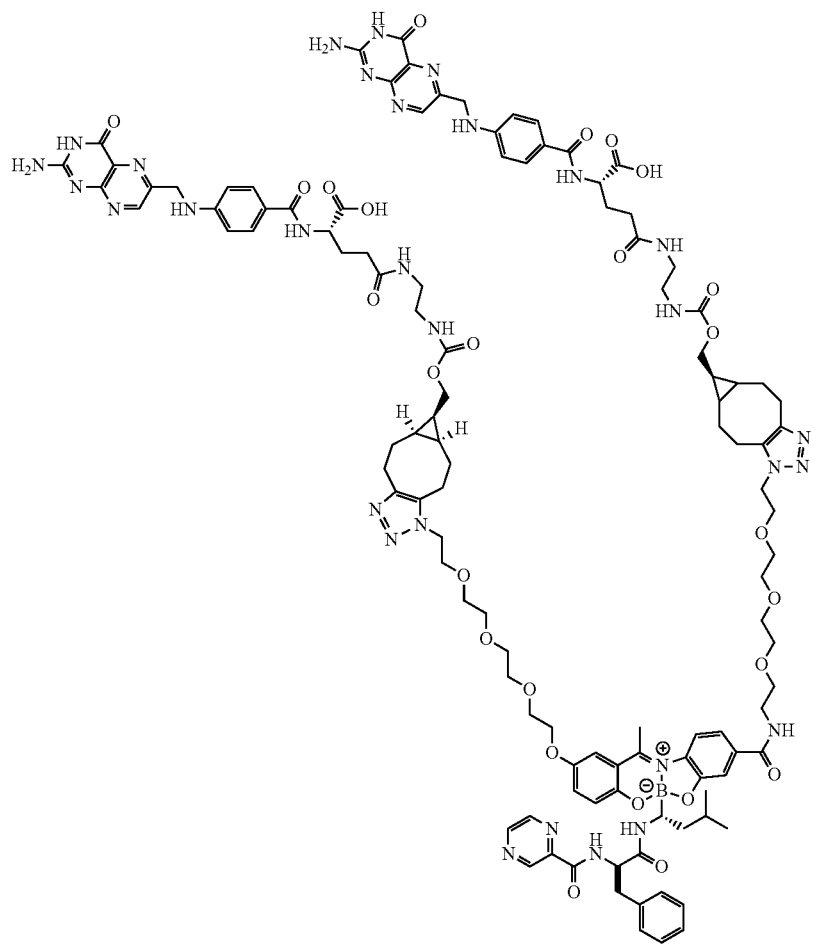
10

-continued
11
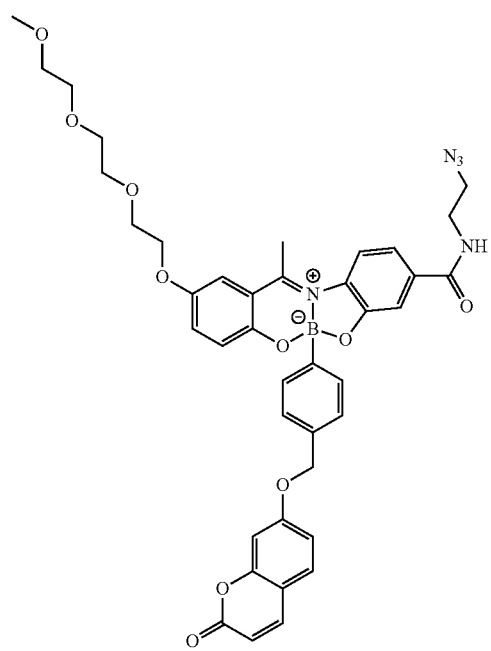
12
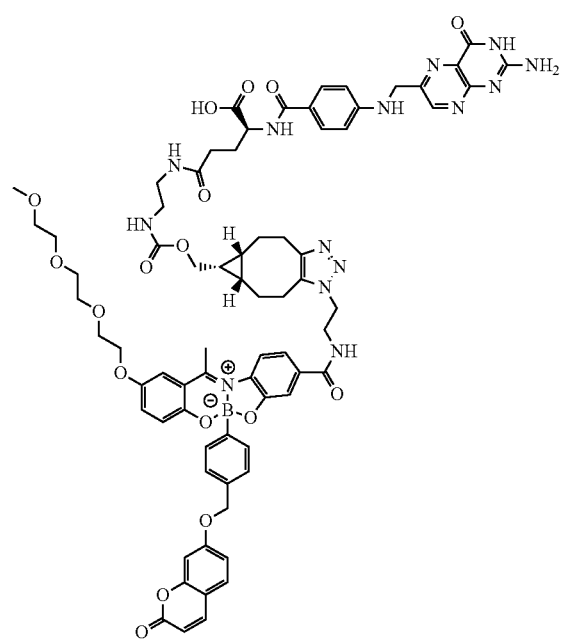
13
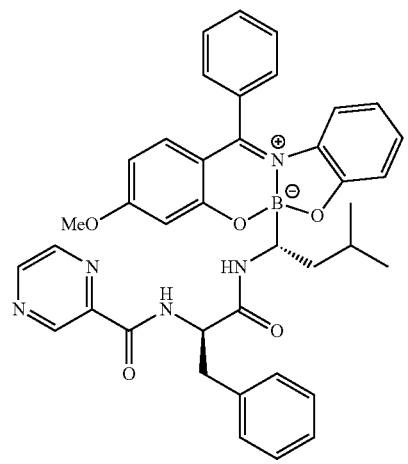
14
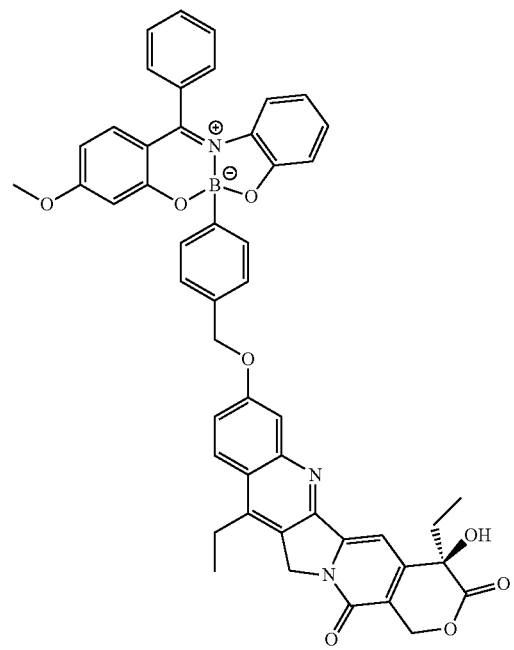

-continued
15
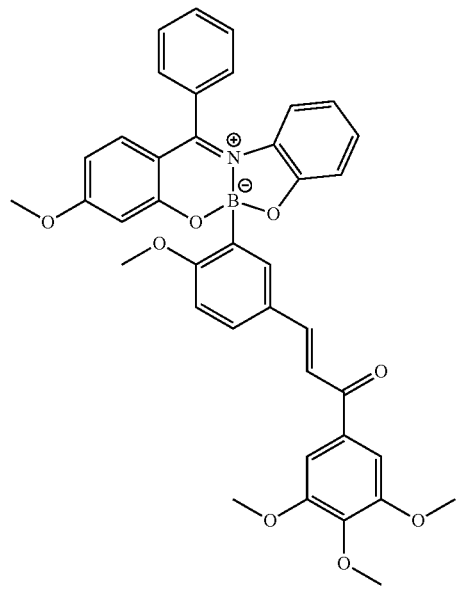
16
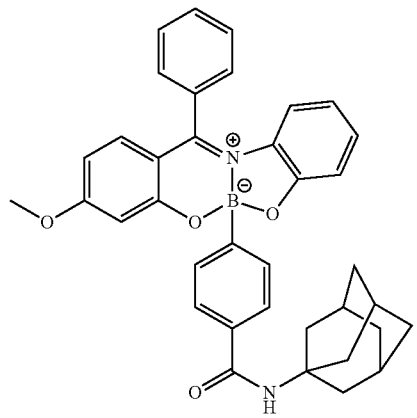
17
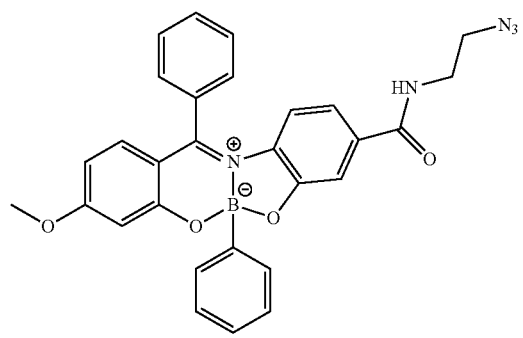
18 a-c
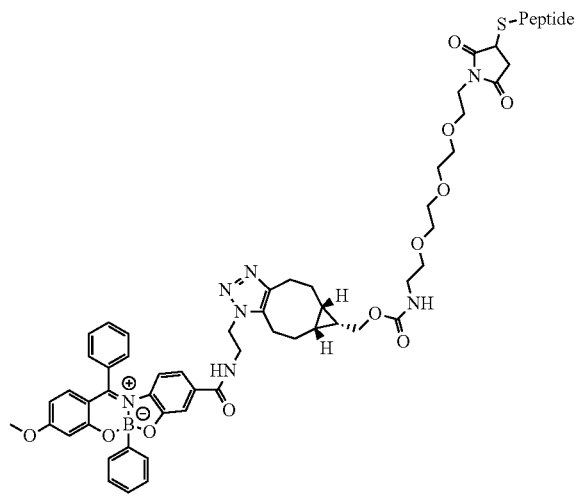
Peptides - a) Lamini; b) Ovalbumine; c) RGD
19
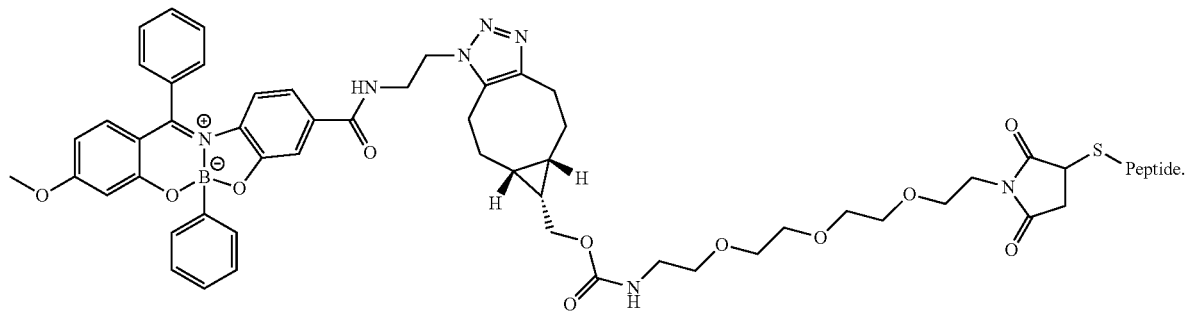

8. The pharmaceutical composition comprising a multifunctional compound as claimed in claim 1, together with a pharmaceutically acceptable carrier therefor.

9. The multifunctional compound as claimed in claim 1 and comprising at least one therapeutically useful cargo molecule or a pharmaceutical composition thereof for use as a medicament.

10. The multifunctional compound as claimed in claim 1 comprising at least one therapeutically useful cargo molecule or a pharmaceutical composition thereof, wherein therapeutic cargo is releasable on contact with a stimulus.

11. The process for the preparation of a multifunctional compound as claimed in claim 1, which process comprises mixing together under reaction conditions at least three component compounds, which component compounds are adapted to covalently bond to form a complex having a tripodal boronated core and one or more substituents selected from:
(a) at least one therapeutically useful cargo molecule or a residue thereof;
(b) at least one water-soluble moiety or a residue of a water-soluble molecule;
(c) at least one functionalizing moiety capable of being post-functionalised with a targeting unit or a residue of a targeting molecule; and/or
(d) at least one targeting unit or a residue of a targeting molecule;
in which any residue of a molecule is such that, on breaking at least one covalent bond of the multifunctional compound, the complete molecule is released; and
wherein the process optionally further comprises a post-functionalisation step, during which at least one functionalizing moiety is substituted by a targeting unit.

12. The multifunctional compound as claimed in claim 3, wherein $R_3$ is a residue of a water-soluble moiety and/or a functionalising moiety and/or a targeting moiety and the residue of a water-soluble moiety and/or a functionalising moiety and/or a targeting moiety is $R_x$-[—O—(—CH$_2$)$_2$-]$_3$—O— in which $R_x$ is a $C_{1-6}$ alkyl chain.

13. The multifunctional compound as claimed in claim 12, wherein the $C_{1-6}$ alkyl chain is end-substituted by either an azide (N$_3$) group or a folate moiety.

14. The multifunctional compound as claimed in claim 13, wherein the folate moiety is a folate-cyclo-octyne derived from N2-(4-(((2-amino-4-oxo-3,4-dihydropteridin-6-yl)methyl)amino)benzoyl)-N5-(2-(((((1R,8S,9s)-bicyclo[6.1.0]non-4-yn-9 yl)methoxy)carbonyl)amino) ethyl)-L-glutamine.

15. The multifunctional compound as claimed in claim 3, wherein $R_7$ is a residue of a therapeutically useful cargo water-soluble moiety and/or a functionalising moiety and/or a targeting moiety and the residue of a therapeutically useful cargo water-soluble moiety and/or a functionalising moiety and/or a targeting moiety is $C_{n=1-6}$ alkyl amide terminating in either an azide (N$_3$) group or a folate moiety.

16. The multifunctional compound as claimed in claim 15, wherein the folate moiety is a folate-cyclo-octyne derived from N2-(4-(((2-amino-4-oxo-3,4-dihydropteridin-6-yl)methyl) amino)benzoyl)-N5-(2-(((((1R,8 S,9s)-bicyclo[6.1.0]non-4-yn-9-yl)methoxy)carbonyl)amino) ethyl)-L-glutamine; or ((1R,8S,9s)-bicyclo[6.1.0]non-4-yn-9-yl) methyl(2-(2-(2-(2-(2,5-dioxo-2,5-dihydro-1H-pyrrol-1-yl) ethoxy)ethoxy)ethoxy)ethyl)carbamate.

17. The multifunctional compound as claimed in claim 3, wherein $R_{10}$ is a residue of an API and the residue of an API is bortezomib, SN38, chalcone or adamantylamine.

18. The multifunctional compound as claimed in claim 5, wherein the targeting unit is selected from small vitamins, peptides, proteins, or enzyme inhibitors.

19. A multifunctional compound comprising a tripodal boranated core, wherein the multifunctional compound further comprises:
(a) at least one therapeutically useful cargo molecule, or a residue thereof;
(b) at least one water-soluble moiety or a residue of a water-soluble molecule; and at least one of components (c) or (d), wherein
(c) is at least one functionalizing moiety capable of being post-functionalised with a targeting unit or a residue of a targeting molecule; and
(d) is at least one targeting unit or a residue of a targeting molecule;
in which any residue of a molecule is such that, on breaking at least one covalent bond of the multifunctional compound, the complete molecule is released; and
wherein the tripodal boronated core is as defined in the general formula:

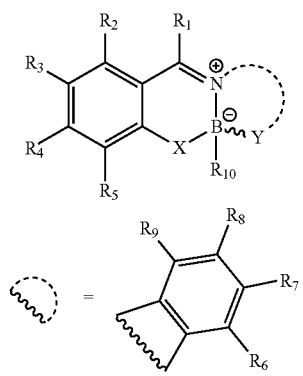

wherein:
$R_1$ is H, $C_{n=1-6}$ alkyl or phenyl;
$R_2$ is H;
$R_3$ is a residue of a water-soluble moiety and/or a functionalising moiety and/or a targeting moiety and the residue of a water-soluble moiety and/or a functionalising moiety and/or a targeting moiety is $R_x$-[—O—(—CH$_2$)$_2$-]$_3$—O— in which $R_x$ is a $C_{1-6}$ alkyl chain;
$R_4$ is H or alkoxy;
$R_5$ and $R_6$ are H;
$R_7$ is H, or is or includes the residue of a therapeutically useful cargo water-soluble moiety and/or a functionalising moiety and/or a targeting moiety;
$R_8$ and $R_9$ are both H;
$R_{10}$ is phenyl, or the residue of a therapeutically useful cargo or a residue of an API; and
X and/or Y is O.

20. A multifunctional compound comprising a tripodal boronated core, wherein the multifunctional compound further comprises:
(a) at least one therapeutically useful cargo molecule, or a residue thereof;
(b) at least one water-soluble moiety or a residue of a water-soluble molecule; and at least one of components (c) or (d), wherein
(c) is at least one functionalizing moiety capable of being post-functionalised with a targeting unit or a residue of a targeting molecule; and (d) is at least one targeting unit or a residue of a targeting molecule;

in which any residue of a molecule is such that, on breaking at least one covalent bond of the multifunctional compound, the complete molecule is released; and wherein the tripodal boronated core is as defined in the general formula:

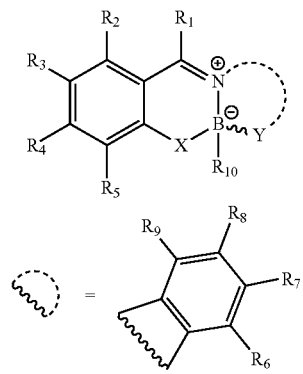

wherein:

$R_1$ is H, $C_{n=1-6}$ alkyl or phenyl;

$R_2$ is H;

$R_3$ is H, or is or includes the residue of a water-soluble moiety and/or a functionalising moiety and/or a targeting moiety;

$R_4$ is H or alkoxy;

$R_5$ and $R_6$ re H;

$R_7$ is a residue of a therapeutically useful cargo water-soluble moiety and/or a functionalising moiety and/or a targeting moiety and the residue of a therapeutically useful cargo water-soluble moiety and/or a functionalising moiety and/or a targeting moiety is $C_{n=1-6}$ alkyl amide terminating in either an azide ($N_3$) group or a folate moiety;

$R_8$ and $R_9$ are both H;

$R_{10}$ is phenyl, or the residue of a therapeutically useful cargo or a residue of an API; and X and/or Y is O.

21. A multifunctional compound comprising a tripodal boranated core, wherein the multifunctional compound further comprises:

(a) at least one therapeutically useful cargo molecule, or a residue thereof;

(b) at least one water-soluble moiety or a residue of a water-soluble molecule; and at least one of components (c) or (d), wherein (c) is at least one functionalizing moiety capable of being post-functionalised with a targeting unit or a residue of a targeting molecule; and (d) is at least one targeting unit or a residue of a targeting molecule;

in which any residue of a molecule is such that, on breaking at least one covalent bond of the multifunctional compound, the complete molecule is released; and wherein the tripodal boronated core is as defined in the general formula:

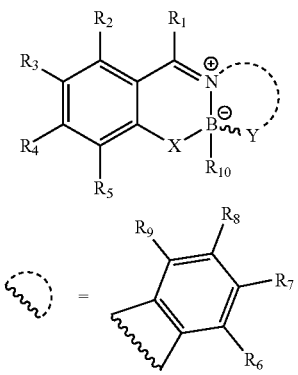

wherein:

$R_1$ is H, $C_{n=1-6}$ alkyl or phenyl;

$R_2$ is H;

$R_3$ is H, or is or includes the residue of a water-soluble moiety and/or a functionalising moiety and/or a targeting moiety;

$R_4$ is H or alkoxy;

$R_5$ and $R_6$ are H;

$R_7$ is H, or is or includes the residue of a therapeutically useful cargo water-soluble moiety and/or a functionalising moiety and/or a targeting moiety;

$R_8$ and $R_9$ are both H;

$R_{10}$ is a residue of an API and the residue of an API is bortezomib, SN38, chalcone or adamantylamine; and X and/or Y is O.

* * * * *